(12) United States Patent
Uchida et al.

(10) Patent No.: US 11,873,226 B2
(45) Date of Patent: Jan. 16, 2024

(54) SHEET-LIKE PARTICLES OF ZEOLITE AND METHOD FOR PRODUCING SAME

(71) Applicant: JAPAN SCIENCE AND TECHNOLOGY AGENCY, Kawaguchi (JP)

(72) Inventors: Yoshiaki Uchida, Kyoto (JP); Koki Sasaki, Ikeda (JP); Norikazu Nishiyama, Minoh (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 102 days.

(21) Appl. No.: 17/617,028

(22) PCT Filed: Jun. 11, 2020

(86) PCT No.: PCT/JP2020/023067
§ 371 (c)(1),
(2) Date: Dec. 7, 2021

(87) PCT Pub. No.: WO2020/250985
PCT Pub. Date: Dec. 17, 2020

(65) Prior Publication Data
US 2022/0332594 A1    Oct. 20, 2022

(30) Foreign Application Priority Data

Jun. 14, 2019 (JP) .................................. 2019-111523

(51) Int. Cl.
*B01J 20/18* (2006.01)
*C01B 39/48* (2006.01)
*C01B 39/28* (2006.01)

(52) U.S. Cl.
CPC ............ *C01B 39/48* (2013.01); *C01B 39/28* (2013.01); *C01P 2002/01* (2013.01); *C01P 2002/74* (2013.01); *C01P 2002/85* (2013.01); *C01P 2004/04* (2013.01)

(58) Field of Classification Search
None
See application file for complete search history.

(56) References Cited

U.S. PATENT DOCUMENTS

| | | | |
|---|---|---|---|
| 2014/0356280 A1 | 12/2014 | Ouyang et al. | |
| 2019/0247825 A1 | 8/2019 | Uchida et al. | |
| 2019/0382274 A1* | 12/2019 | Winter | ...................... C08L 9/00 |

FOREIGN PATENT DOCUMENTS

| | | | |
|---|---|---|---|
| CN | 106256764 A | | 12/2016 |
| CN | 107697929 | * | 2/2018 |
| CN | 108975345 A | | 12/2018 |
| JP | H11-092769 A | | 4/1999 |
| JP | 2001114511 A | | 4/2001 |
| JP | 2004503378 A | | 2/2004 |
| JP | 2011502777 A | | 1/2011 |
| JP | 2012530680 A | | 12/2012 |
| JP | 2016-104690 A | | 6/2016 |
| KR | 20080099607 | * | 11/2008 |
| WO | 0205950 A2 | | 1/2002 |
| WO | 2007/119728 A1 | | 10/2007 |
| WO | 2009065877 A1 | | 5/2009 |
| WO | 2010150996 A2 | | 12/2010 |
| WO | 2018016650 A1 | | 1/2018 |
| WO | 2018025104 A1 | | 2/2018 |

OTHER PUBLICATIONS

International Search Report (PCT/ISA/210) with an English translation, and Written Opinion (PCT/ISA/237) dated Aug. 25, 2020, by the Japanese Patent Office as the International Searching Authority for International Application No. PCT/JP2020/023067. (17 pages).
Přech, Jan, et al., "Synthesis and Post-Synthesis Modification of Novel 2-Dimensional Zeolites", Dissertation Thesis, Charles University, Faculty of Science, Department of Physics and Macromolecular Chemistry, Prague, Czech Republic, Oct. 2016, pp. 1-61. (61 pages).
Sasaki, Koki, et al., "New Synthesis Method of Zeolite Nanosheets in Hyperswollen Lyotropic Lamellar Phase", The Japanese Liquid Crystal Society Conference Program, Sep. 4-6, 2019, University of Tsukuba, Japan, 1A04. (4 pages).
Sasaki, Koki, et al., "Novel synthesis method of nanosheets by using two-dimensional reactors in amphiphilic phases", International Symposium for Nano Science (ISNS 2019) Program, Osaka University, Osaka, Japan, Nov. 27-28, 2019, p. 34. (5 pages).
Sasaki, Koki, et al., "Synthesis of Aluminosilicate Nanosheets using TRAP Method as a Precursor of CHA-Type Zeolite Nanosheets", 18th Asian Pacific Confederation of Chemical Engineering Congress (APCChE), The Society of Chemical Engineers, Sapporo, Japan, Sep. 23-27, 2019. (4 pages).
Sasaki, Koki, et al., "Versatile synthesis method of nanosheets: TRAP method", 18th Asian Pacific Confederation of Chemical Engineering Congress (APCChE), The Society of Chemical Engineers, Sapporo, Japan, Sep. 23-27, 2019, C405. (3 pages).
Uchida, Yoshiaki, et al., "Nanosheet Formation in Hyperswollen Lyotropic Lamellar Phases", Journal of the Japanese Liquid Crystal Society, EKISHO, 2018, vol. 22, No. 1, pp. 37-42. (8 pages).
Office Action dated Jun. 8, 2023, by the China National Intellectual Property Administration in corresponding Chinese Patent Application No. 202080042234.6, with an English translation of the Office Action (23 pages).

* cited by examiner

*Primary Examiner* — Sheng H Davis
(74) *Attorney, Agent, or Firm* — BUCHANAN INGERSOLL & ROONEY PC

(57) ABSTRACT

The invention provides a method for producing sheet-like particles of zeolite that cannot be obtained by a top-down method, and provides sheet-like particles of zeolite having an 8-membered oxygen ring structure obtained by the method. A thickness of the sheet-like particles is 1 nm to 100 nm, and an aspect ratio (maximum width/thickness in particles) of the sheet-like particles is 100 or more.

8 Claims, 26 Drawing Sheets

SHEET-LIKE PARTICLES OF ZEOLITE AND METHOD FOR PRODUCING SAME

TECHNICAL FIELD

The invention provides sheet-like particles of zeolite and a method for producing the same.

The present application claims priority under Japanese Patent Application No. 2019-111523 filed on Jun. 14, 2019, the contents of which are incorporated herein.

BACKGROUND TECHNOLOGY

Zeolite is a compound having a regularly arranged pore structure, and has adsorption separation ability, ion exchange ability, shape selection ability, and the like because of its unique structure, and is widely used in industry.

Although various methods for producing zeolite have been reported, zeolite is generally produced by a hydrothermal synthesis method.

In the hydrothermal synthesis method, a gel-like substance or a slurry-like substance is prepared by mixing a raw material of zeolite with liquid water, and the prepared gel-like substance or slurry-like substance is heated under a predetermined pressure condition to deposit a crystal of zeolite. Crystals of zeolite obtained by the hydrothermal synthesis method are separated from liquid water contained in the gel-like substance or the slurry-like substance by performing operations such as centrifugation and decantation.

As a method for producing zeolite other than the hydrothermal synthesis method, a dry gel conversion (DGC) method is used. The method includes drying a gel-like substance obtained by mixing a raw material of zeolite with water, and bringing the obtained dried gel into contact with gaseous water in a container in the presence of a structure-directing agent (for example, see Patent Document 1).

Zeolite is often used as a high-performance catalyst in petrochemistry and synthetic chemistry. However, in spite of its potential as a high-performance catalyst, there has been a problem in that the catalyst is deactivated because the pores are rapidly clogged with by-products. As a method for solving the problem, a thin sheet-like zeolite (zeolite nanosheet) having a thickness of 1 to 100 nm is proposed. As a method for synthesizing the zeolite nanosheet, a method for obtaining the nanosheet by exfoliating the zeolite having a layered structure (top-down method) and a method for synthesizing the zeolite nanosheet using an appropriately designed bifunctional surfactant (bottom-up method) have been proposed. For example, in the bottom-up method, an MFI-type zeolite nanosheet and an MTW-type zeolite nanosheet are disclosed (for example, see Patent Document 2).

On the other hand, various methods for producing the nanosheet have been studied. For example, when a bilayer forms a hyper-swollen lamellar phase in a solvent, a sheet-like metal organic structure is formed between two monolayers constituting one bilayer to provide a method for producing a metal organic structure nanosheet (for example, see Patent Document 3).

PATENT DOCUMENTS

[Patent Document 1] Japanese Unexamined Patent Application Publication No. 2001-114511

[Patent Document 2] Japanese Translation of PCT International Application Publication No. 2012-530680

[Patent Document 3] WO2018/016650

SUMMARY OF THE INVENTION

Problem to be Solved by the Invention

However, the zeolite nanosheets can be formed by the top-down method using the layered zeolite as a raw material, but there is a problem in that the nanosheets are agglomerated. Further, when the crystal structure of a target zeolite is not layered, the zeolite nanosheet cannot be produced by the top-down method. In the bottom-up method described in Patent Document 2, since it is optimized for a specific zeolite, it is limited to MFI-type and MTW-type zeolite nanosheets. There are no examples of producing zeolite nanosheets of other crystal structures via this method.

In addition, there is no disclosure about zeolite nanosheets in Patent Document 3, and in particular, there is no disclosure about a method for producing zeolite nanosheets having various crystal structures.

It is an object of the present invention to provide a method for producing zeolite nanosheets having various crystal structures. It is another object of the present invention to provide sheet-like particles of zeolite having an 8-membered oxygen ring structure, and especially zeolite nanosheets having CHA, SOD, or PHI crystal structures.

Means for Solving Problems

The present invention provides the following means for solving the above problems.

[1] Sheet-like particles of zeolite having an 8-membered oxygen ring structure,
wherein a thickness of the sheet-like particles is 1 nm or more and 100 nm or less, and
an aspect ratio (maximum particle width/particle thickness) of the sheet-like particles is 100 or more.

[2] The sheet-like particles of zeolite according to [1],
wherein a plurality of the sheet-like particles of zeolite are present, and
the sheet-like particles are present in a state in which the sheet-like particles are not substantially agglomerated.

[3] The sheet-like particles of zeolite according to [1] or [2], which have a structure represented by "CHA" which is a structural code of the International Zeolite Association (IZA),
wherein the thickness of the sheet-like particles is 1 nm or more and 20 nm or less, and
the aspect ratio (maximum particle width/particle thickness) of the sheet-like particles is 100 or more.

[4] The sheet-like particles of zeolite according to [1] or [2], which have a structure represented by the structural code "PHI" of the International Zeolite Association (IZA),
wherein the thickness of the sheet-like particles is 1 nm or more and 100 nm or less, and
the aspect ratio (maximum particle width/particle thickness) of the sheet-like particles is 100 or more.

[5] The sheet-like particles of zeolite according to [1] or [2], which have a structure represented by the structural code "SOD" of the International Zeolite Association (IZA),
wherein the thickness of the sheet-like particles is 1 nm or more and 100 nm or less, and
the aspect ratio (maximum particle width/particle thickness) of the sheet-like particles is 100 or more.

[6] A method for producing sheet-like particles of zeolite, comprising:
a first step which comprises
forming a bilayer in a solvent,
forming a hyper-swollen lamellar phase of the bilayer by adding, in the solvent, an aluminum atomic source, and at least one atomic source selected from the group consisting of a silicon atomic source and a phosphorus atomic source, and
forming sheet-like particles of a precursor of zeolite between two monomolecular layers constituting one bilayer; and
a second step of bringing the sheet-like particles of the precursor of zeolite into contact with gaseous water in a container to form the sheet-like particles of zeolite.

[7] The method for producing the sheet-like particles of zeolite according to [6],
wherein a mass ratio of the solvent to whole system in formation of the hyper-swollen lamellar phase is 90% by mass or more.

[8] The method for producing the sheet-like particles of zeolite according to [6],
wherein the solvent contained in a system for forming the hyper-swollen lamellar phase is a mixed solvent containing a hydrocarbon-based solvent and water, and
a mass ratio of the hydrocarbon-based solvent and water in the mixed solvent is 85:15 to 99.99:0.01.

[9] The method for producing the sheet-like particles of zeolite according to [8],
wherein an amount of water contained in the solvent is 5% by mass or less.

[10] The method for producing the sheet-like particles of zeolite according to any one of [6] to [9],
wherein in the second step, contacting with gaseous water is carried out in the presence of a structure-directing agent.

[11] The method for producing the sheet-like particles of zeolite according to any one of [6] to [10],
wherein the sheet-like particles of zeolite have a structure represented by "SOD", "PHI", "CHA", or "MFI", each of which is a structural code of the International Zeolite Association (IZA).

[12] The method for producing the sheet-like particles of zeolite according to any one of [6] to [11],
wherein the sheet-like particles of the precursor of zeolite are present in a hyper-swollen lamellar phase in a state where the sheet-like particles are not substantially agglomerated.

[13] The method for producing the sheet-like particles of zeolite according to any one of [6] to [12],
wherein a thickness of the sheet-like particles of the precursor of zeolite is 1 nm or more and 100 nm or less, and
an aspect ratio (maximum particle width/particle thickness) of the sheet-like particles of the precursor of zeolite is 100 or more.

[14] The method for producing the sheet-like particles of zeolite according to any one of [6] to [13],
wherein a thickness of the sheet-like particles of the zeolite is 1 nm or more and 100 nm or less, and
an aspect ratio (maximum width/thickness in particles) of the sheet-like particles of the zeolite is 100 or more.

[15] The method according to any one of [6] to [14], wherein the zeolite is aluminosilicate.

[16] A catalyst composition for a membrane reactor, comprising the sheet-like particles of zeolite of any one of claims 1 to 5 as a reaction-activation component.

[17] The catalyst composition for the membrane reactor according to [16],
wherein the reaction to be activated is at least one reaction selected from the group consisting of an ATO reaction, an MTO reaction, a PPTO reaction, and a PLTO reaction, and
the ATO reaction, the MTO reaction, the PPTO reaction, and the PLTO reaction mean a reaction of acetone to olefins, a reaction of methanol to olefins, a reaction of propane to olefins, and a reaction of propylene to olefins, respectively.

[18] A catalyst additive for cracking waste plastic containing the sheet-like particles of zeolite of any one of [1] to [5] as a reaction-activation component.

[19] A method for recycling waste plastic, comprising:
mixing waste plastic with the sheet-like particles of zeolite of any one of [1] to [5] as a reaction-activation component; and
thermally decomposing a mixture obtained in the mixing step.

Effect of the Invention

Sheet-like particles of zeolite which have an 8-membered oxygen ring structure and which cannot be obtained by a top-down method can be provided. Further, a method for producing sheet-like particles of zeolite that cannot be obtained by a top-down method can be provided. In particular, zeolite nanosheets and a method for producing the same in a stable manner without aggregation can be provided.

("NSs": Examples using zeolite nanosheets; "Bulk": A comparative example using zeolite (CHA type) as a bulk sample. The same applies to FIGS. 30, 32, and 34.)

Figure 29:
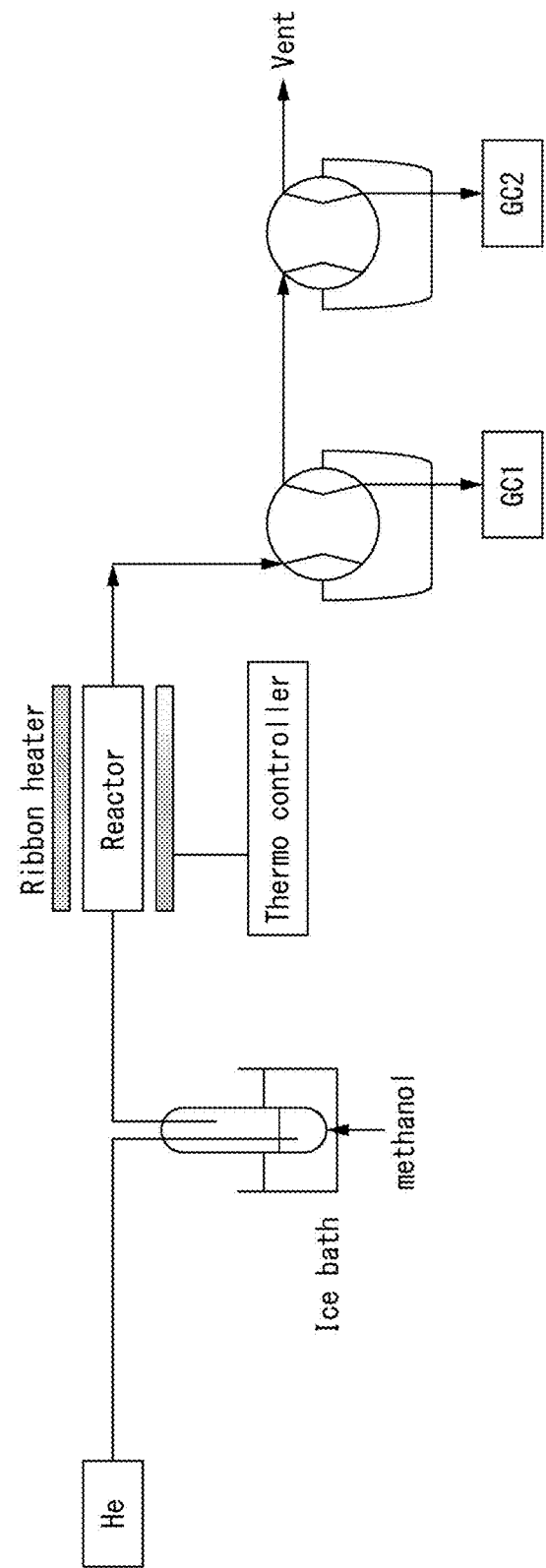

FIG. 29 is a schematic diagram showing a gas line for the reaction of methanol with olefins.

Figure 30:
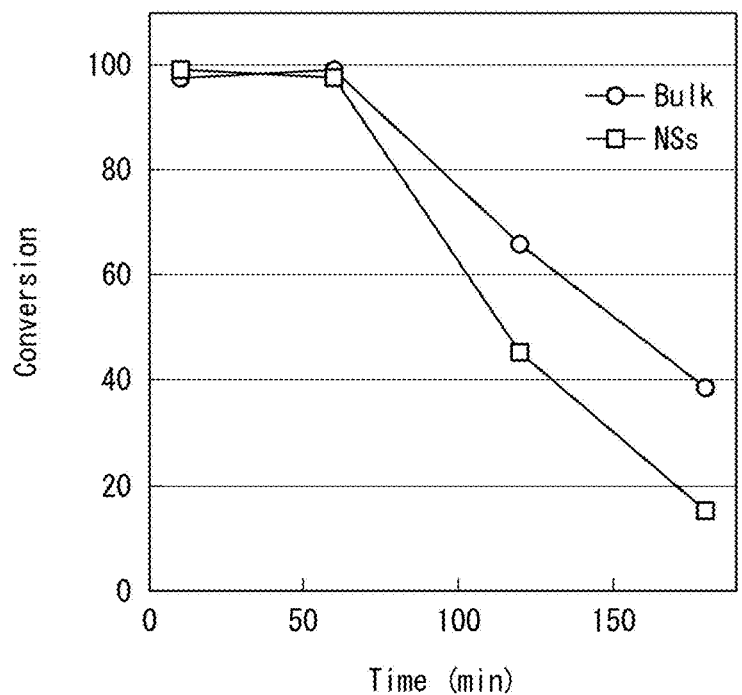

FIG. 30 shows the time courses of the methanol conversion reactions of CHA-type zeolite nanosheets and bulk samples.

Figure 31:
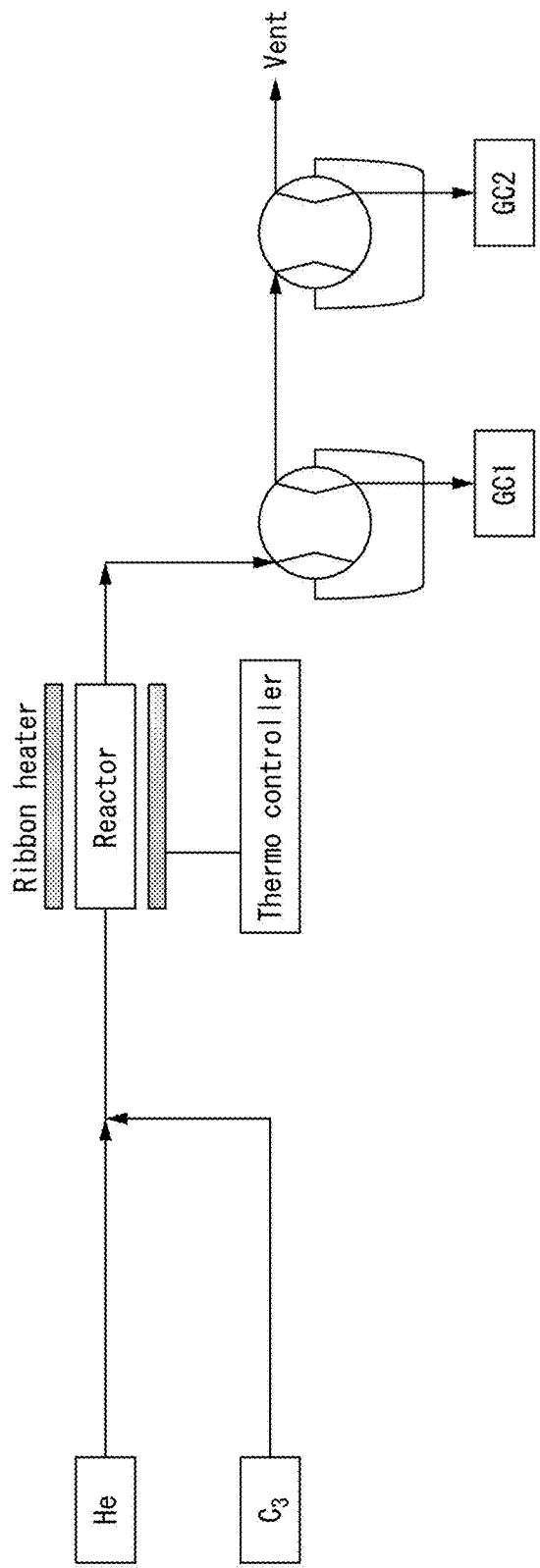

FIG. 31 is a schematic diagram showing a propane-olefin reaction gas line.

Figure 32:
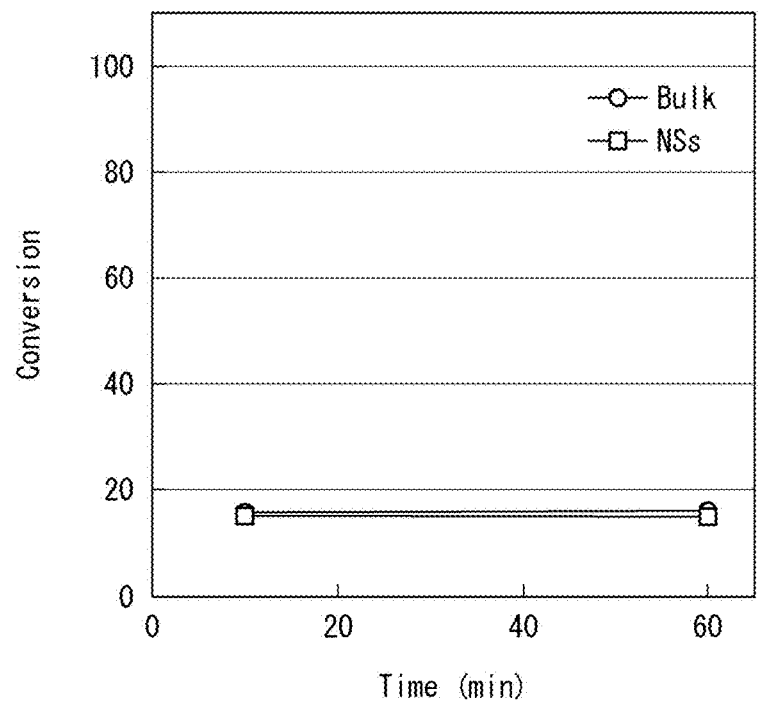

FIG. 32 shows the time courses of the propane conversion reactions of CHA-type zeolite nanosheets and bulk samples.

Figure 33:
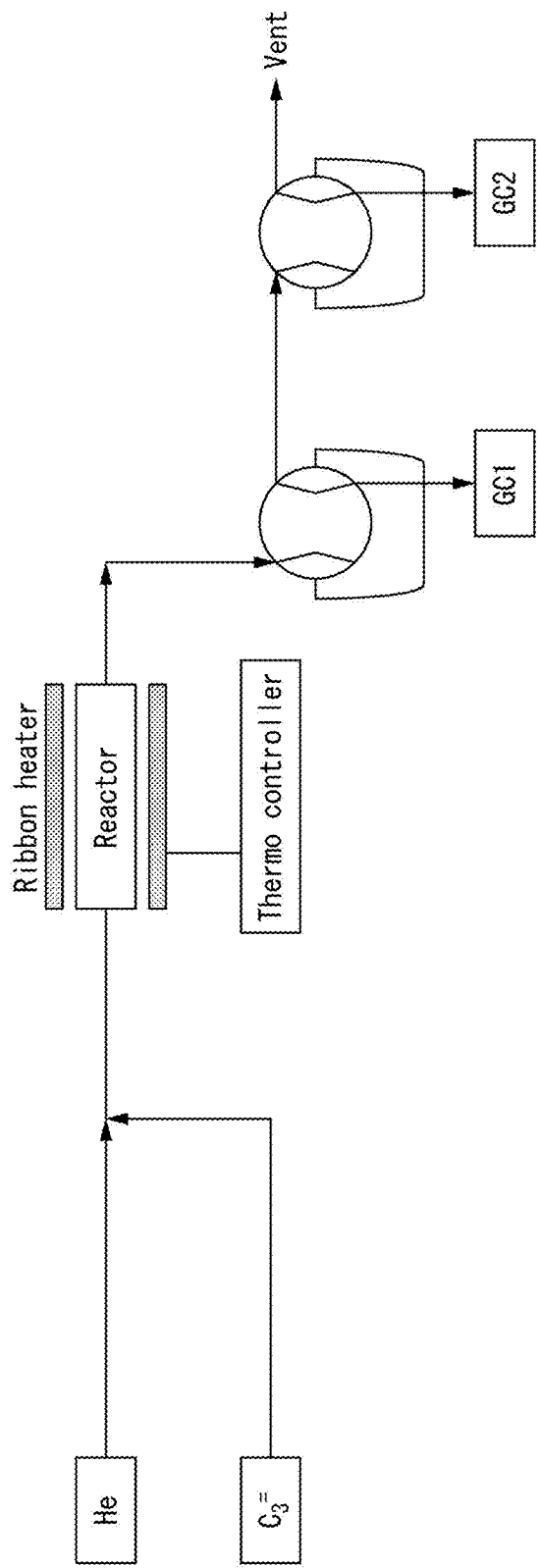

FIG. 33 is a schematic diagram showing a propylene-olefin reaction gas line.

Figure 34:
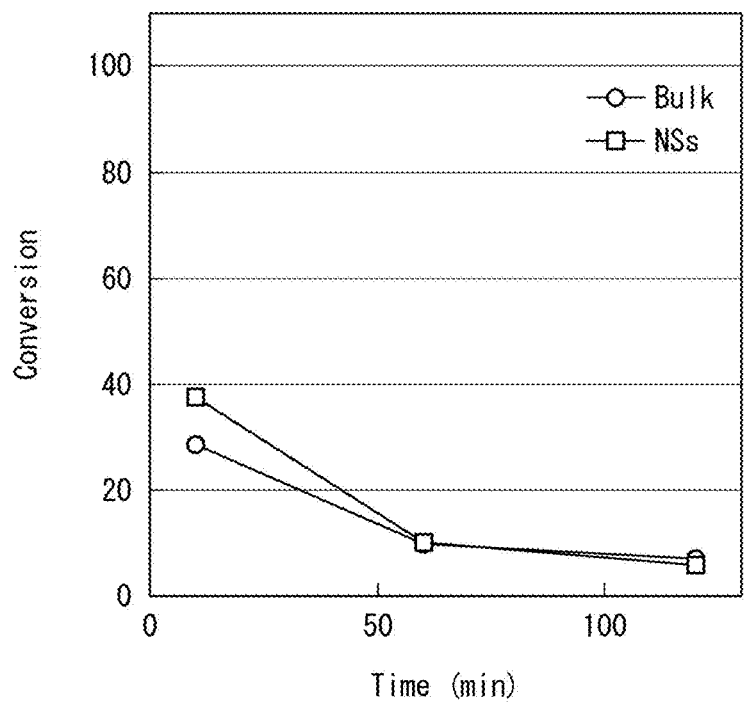

FIG. 34 shows the time courses of the propylene conversion reactions of CHA-type zeolite nanosheets and bulk samples.

Figure 35:
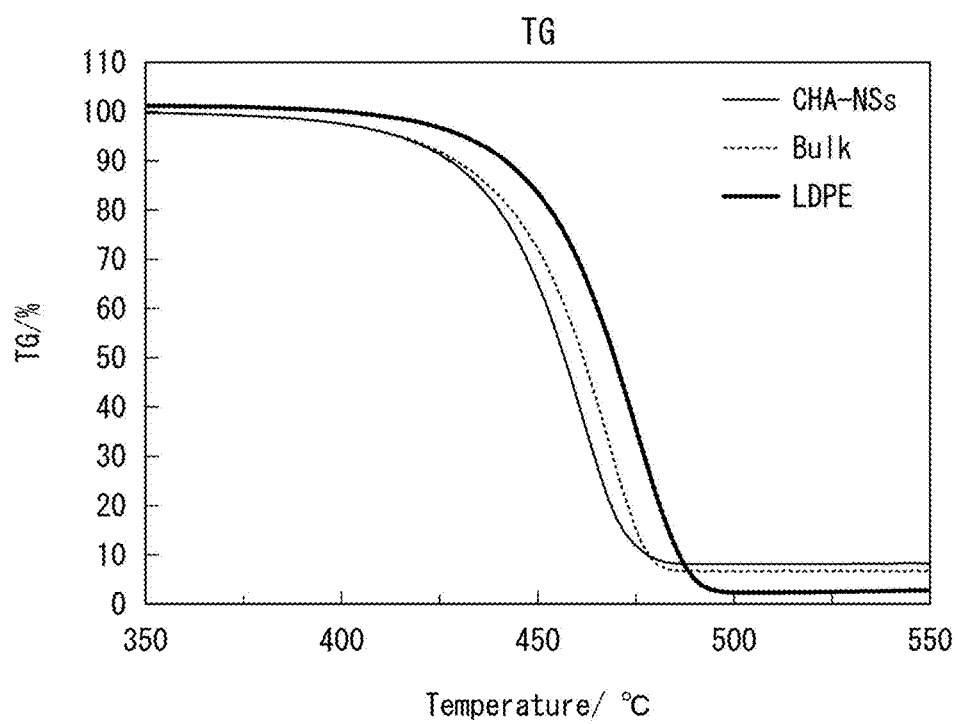

FIG. 35 shows the experimental results of TG showing the effect of lowering polyethylene decomposition temperature via the addition of zeolite nanosheets.

Figure 36:
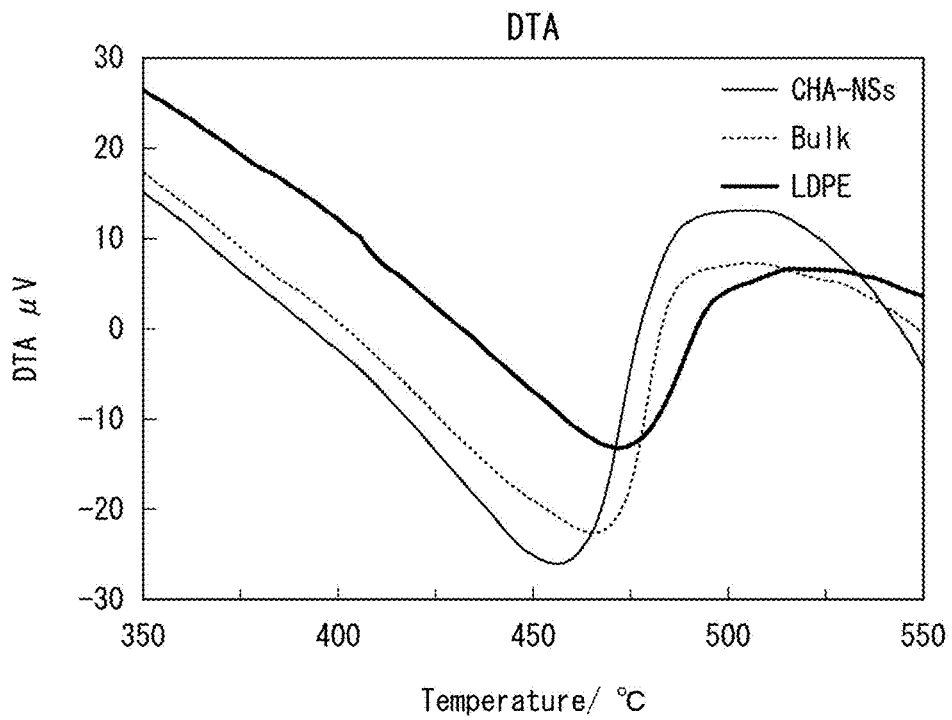

FIG. 36 shows an experimental result of DTA showing the effect of the addition of zeolite nanosheets on lowering the polyethylene degradation temperature.

("CHA-NSs": Example of adding CHA-type zeolite nanosheets to low-density polyethylene (LDPE); "Bulk": Comparative example of adding zeolite (CHA type) of a bulk sample to low-density polyethylene (LDPE); "LDPE": Comparative example of only low-density polyethylene (LDPE) without addition of zeolite. The same applies to FIGS. 37 to 42.)

Figure 37:
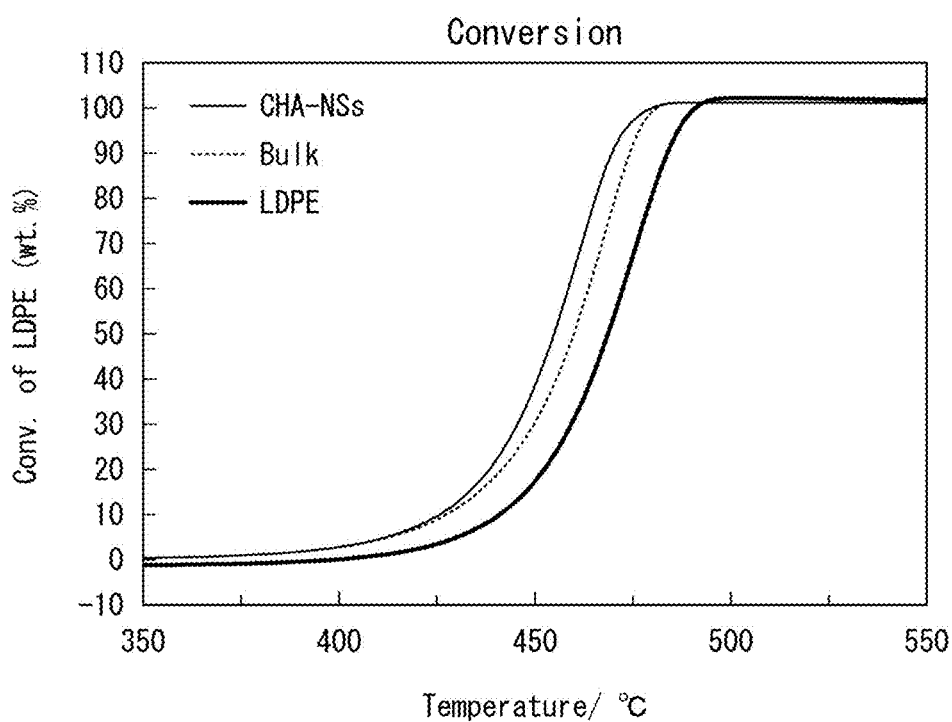

FIG. 37 shows the experimental results of Conversion showing the effect of the addition of zeolite nanosheets on lowering the polyethylene decomposition temperature.

Figure 38:
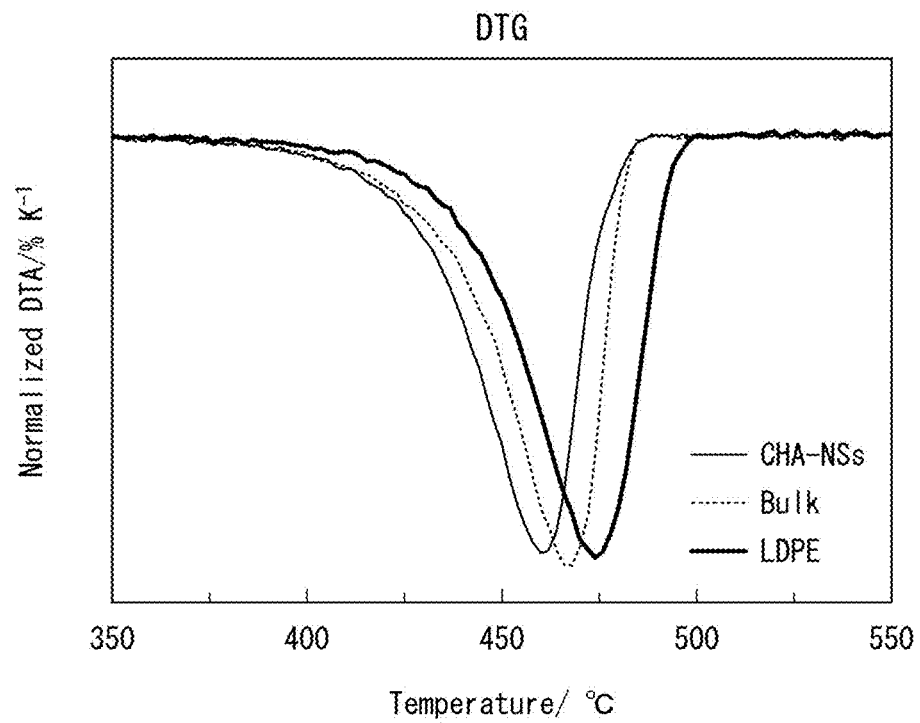

FIG. 38 shows an experimental result of DTG showing the effect of the addition of zeolite nanosheets on lowering the polyethylene degradation temperature.

Figure 39:
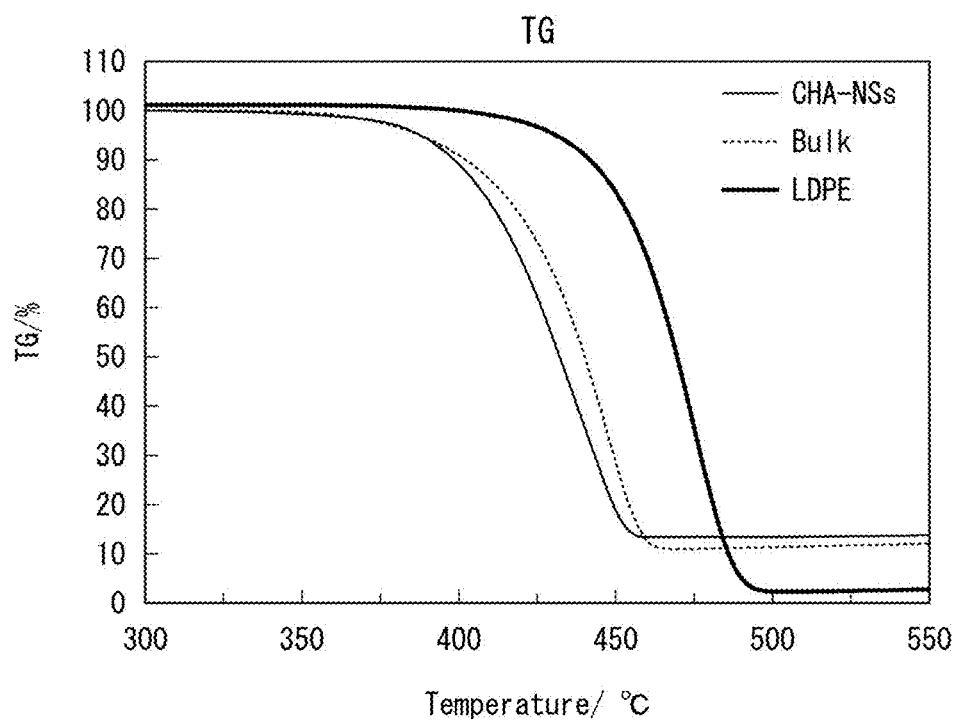

FIG. 39 shows the experimental results of TG showing the effect of the addition of zeolite nanosheets on lowering polyethylene decomposition temperature.

Figure 40:
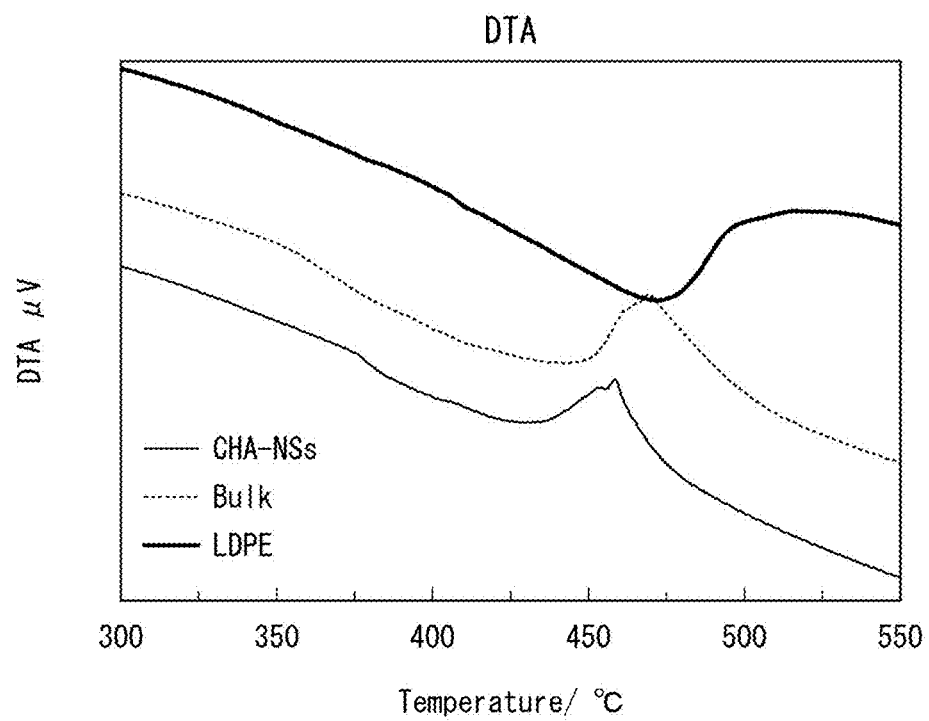

FIG. 40 shows an experimental result of DTA showing the effect of the addition of zeolite nanosheets on lowering polyethylene degradation temperature.

Figure 41:
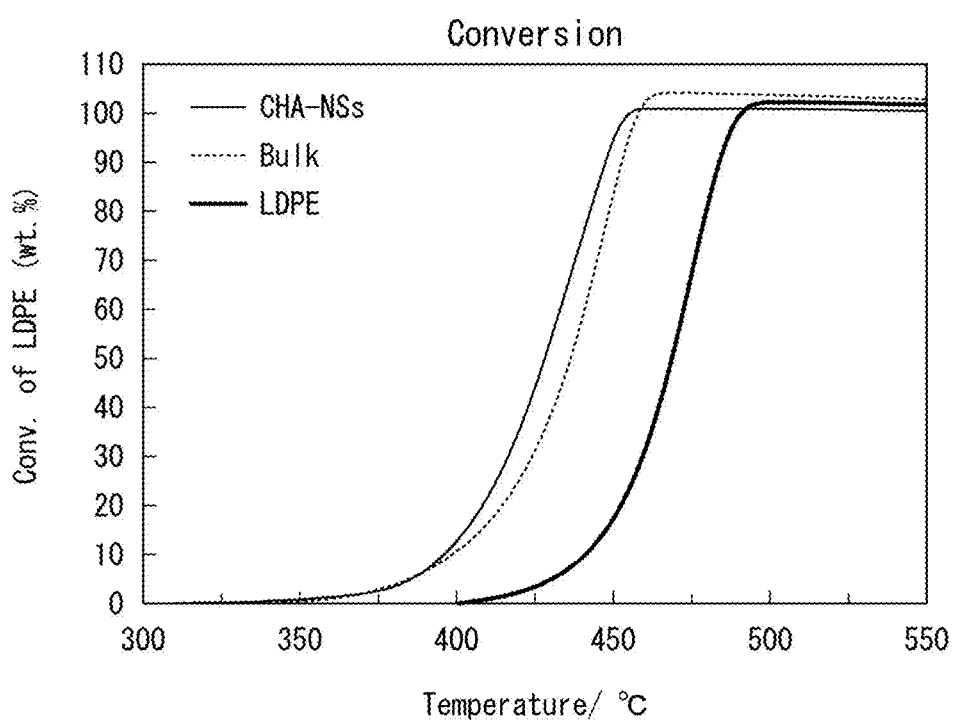

FIG. 41 shows the experimental results of Conversion showing the effect of the addition of zeolite nanosheets on lowering the polyethylene decomposition temperature.

Figure 42:
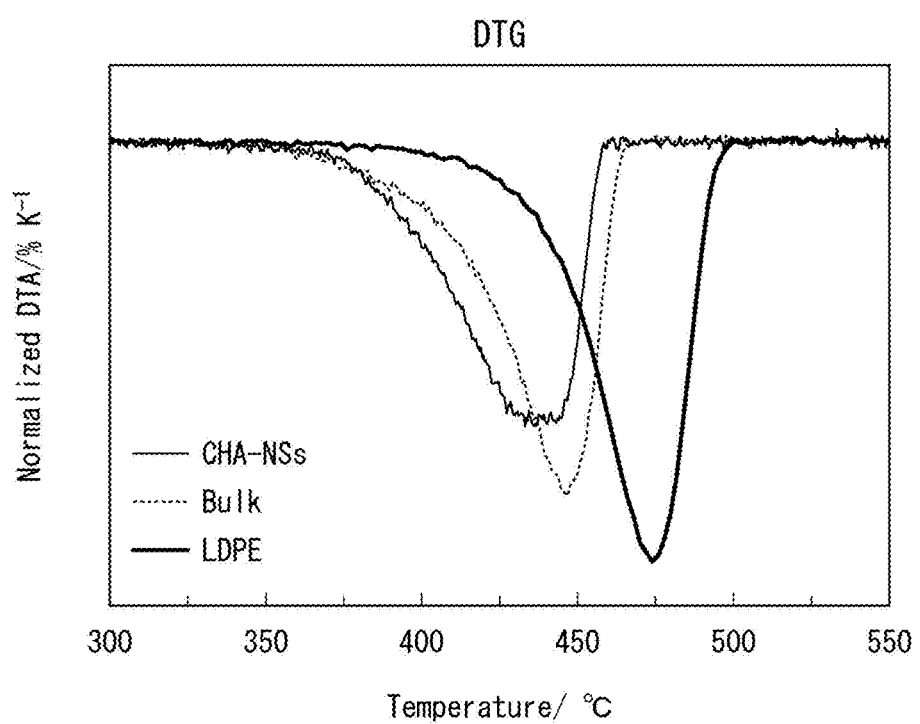

FIG. 42 shows an experimental result of DTG showing the effect of the addition of zeolite nanosheets on lowering the polyethylene degradation temperature.

DETAILED DESCRIPTION OF THE INVENTION

Hereinafter, a method for producing sheet-like particles of zeolite according to an embodiment of the present invention will be described. It is to be noted that the present embodiment is for the purpose of providing a better understanding of the object of the present invention and is not intended to limit the present invention unless otherwise specified.

(Zeolite)

Zeolite is generally a porous crystalline compound having crystallinity and forming open regular micropores (hereinafter sometimes referred to simply as "pores"), and has a structure in which $TO_4$ units (T denotes an element other than oxygen constituting zeolite; examples include Si, Al, P, Ga, etc.) having a tetrahedral structure are three-dimensionally connected by sharing oxygen atoms. These usually correspond to porous crystalline compounds including, for example, aluminosilicate, silicoaluminophosphate, aluminophosphate, and the like.

(Method for Producing Sheet-Like Particles of Zeolite)

The method for producing the sheet-like particles of zeolite according to one embodiment of the present invention (also referred to as the present embodiment) includes a first step for producing sheet-like particles of a precursor of zeolite and a second step for producing sheet-like particles of the zeolite from the sheet-like particles of the precursor.

Here, the "precursor of zeolite" means a compound corresponding to a constituent unit which constitutes zeolite which is a porous crystalline compound. Examples of the precursor of zeolite include aluminosilicate, silicoaluminophosphate, aluminophosphate, and the like. These precursors may be crystalline or amorphous compounds.

Hereinafter, a case where the zeolite is an aluminosilicate will be described in detail as a specific example.

That is, when the zeolite is an aluminosilicate, the method includes a first step of producing sheet-like particles of the aluminosilicate which is a precursor of zeolite, and a second step of producing sheet-like particles of the zeolite from the sheet-like particles of the aluminosilicate.

In the first step, a bilayer is formed in a solvent, an aluminum atom source and at least one or more atom sources selected from the group consisting of a silicon atom source and a phosphorus atom source are added to the solvent to form a hyper-swollen lamellar phase of the bilayer, and the sheet-like particles of aluminosilicate are formed between two monomolecular layers constituting one bilayer.

In the second step, the particles of aluminosilicate are brought into contact with gaseous water in a container.

<First Step>

In the first step, the sheet-like particles of aluminosilicate as a precursor of zeolite are produced by using a hyper-swollen lamellar phase.

In the present embodiment, a hyper-swollen lamellar phase is first formed, and a raw material of aluminosilicate is added. As a method for forming the hyper-swollen lamellar phase, a bilayer is formed in a solvent, and an amphiphilic substance is added to the solvent to form a hyper-swollen lamellar phase of the bilayer.

A hyper-swollen lamellar phase is a specific lamellar phase that is swollen by a solvent. More specifically, it refers to a phase in which a plurality of bilayers constituting a lamellar phase are stacked in layers in the manner of sandwiching a solvent layer between bilayers.

The phase constituting the hyper-swollen lamellar phase is colored by Bragg reflection in the visible light region. The presence of a phase constituting the hyper-swollen lamellar phase may be confirmed by placing an object in a transparent container to which a polarizing film is attached (especially, for example, a transparent container in which a polarizing film is wound with a polarization axis inclined by 45 degrees) and actually visually observing the object. In this case, if the color produced by the birefringence of the object can be observed, the presence of the characteristic optical structure contained in the object can be confirmed. The hyper-swollen lamellar phase may be a hyper-swollen lyotropic lamellar phase.

In the hyper-swollen lamellar phase, a mass ratio of the solvent in the whole system in the formation of the hyper-swollen lamellar phase is not particularly limited as far as the object of the present invention is satisfied, but is usually 90% by mass or more, preferably 95% by mass or more, more preferably 98% by mass or more, and still more preferably 99% by mass or more. The upper limit is not particularly limited as long as it is within a range in which a hyper-swollen lamellar phase can be formed between a solute and a solvent, and the concentration of a limit in which a hyper-swollen lamellar phase can be formed between a solute and a solvent used is a theoretical upper limit. The term "whole" as used above means the sum of all things in a mixture containing a solute and a solvent. In the hyper-swollen lamellar phase, the upper limit of the mass ratio of the solvent to the whole may be, for example, 99% by mass.

In the hyper-swollen lamellar phase, a distance (hereinafter referred to as "interlayer distance") between the adjacent bilayers is not particularly limited, and can be appropriately set depending on the material used and the intended application, but is usually 50 nm or more and 1000 nm or less (including the values at both ends, and hereinafter the same). The interlayer distance is preferably not too thin and not too thick, for example, preferably 100 nm or more and 500 nm or less, in order to satisfy an amount that can be synthesized while maintaining the thickness of the target nanosheet. The interlayer distance between the bilayers means the distance from an end of the solvent-affinity portion of a first bilayer to the end of the solvent-affinity portion of a second bilayer adjacent to the first bilayer. The interlayer distance may depend on the content of molecules (amphiphilic molecules) constituting the bilayer.

The thickness of the bilayer itself is not particularly limited, but is usually 1 nm to 20 nm.

The hyper-swollen lamellar phase is stably maintained even in a solution of a nonionic amphiphile by undulation or Helfrich interaction of each layer.

Sheet-like particles of aluminosilicate can be produced by synthesizing the aluminosilicate inside a bilayer of a hyper-swollen lamellar phase. In particular, aluminosilicate nanosheets can be produced.

After forming a hyper-swollen lamellar phase, a silicon atom source and an aluminum atom source are added to the solvent as raw materials of aluminosilicate to form sheet-like particles of aluminosilicate between two monolayers constituting the one bilayer. A phosphorus atom source and an aluminum atom source may be added as a raw material of the aluminosilicate, and a silicon atom source, a phosphorus atom source, and an aluminum atom source may be added as a raw material of the aluminosilicate.

A molar ratio of the silicon atom source to the aluminum atom source as the composition of the raw material of the aluminosilicate is not particularly limited, and can be suitably set according to the composition ratio of the sheet-like particles of the zeolite to be produced. For example, when the sheet-like particles of CHA-type zeolite are produced, the molar ratio of silicon atom source to aluminum atom source (Si/Al molar ratio) is usually 5 or more and 150 or less, preferably 100 or less, and more preferably 60 or less.

In the method for producing the sheet-like particles of aluminosilicate, the sheet-like particles are formed between the hydrophilic portions of two monolayers constituting one bilayer by turning the hydrophobic portions toward the solvent side. By changing the combination of the solvent to be mixed and the amphiphilic molecule, the hydrophobic part and the hydrophilic part of the bilayer are arranged as described above. In the present disclosure, since the nanosheets are formed between portions that are not compatible with the solvent, the nanosheets may be produced not only in a hydrophilic reaction field but also in a hydrophobic reaction field, depending on the type of solvent.

As the solvent in the present embodiment of the method for producing the sheet-like particles of the aluminosilicates, an organic solvent is preferable. The organic solvent may be a hydrocarbon-based solvent.

Examples of the hydrocarbon-based solvent include an aliphatic hydrocarbon solvent such as cyclohexane, methylcyclohexane, n-pentane, n-hexane, n-heptane, n-octane, n-nonane, n-decane, n-dodecane, and bicyclohexyl; an aromatic hydrocarbon solvent such as toluene, xylene, mesitylene, ethylbenzene, n-hexylbenzene, cyclohexylbenzene, and the like. The solvent may be only a hydrocarbon-based solvent or a combination of a hydrocarbon-based solvent and another organic solvent.

Examples of the other organic solvents include a ketone-based solvent such as acetone, acetylacetone, methyl ethyl ketone, cyclohexanone, or acetophenone; an alcohol-based solvent such as methanol, ethanol, n-propanol, isopropyl alcohol, cyclohexanol, ethylene glycol, diethylene glycol, propylene glycol, and glycerin; a chlorinated solvent such as 1,2-dichloroethane, 1,1,2-trichloroethane, chlorobenzene, and o-dichlorobenzene; an ether-based solvent such as tetrahydrofuran, dioxane, anisole, 4-methylanisole, and the like.

When a hydrocarbon-based solvent and another organic solvent are used as the solvent, a mass ratio of the hydrocarbon-based solvent to the other organic solvent is preferably 80:20 to 99.99:0.01, and more preferably 85:15 to 99.9:0.1.

The solvent in this producing method may contain water. For example, when the solvent contains the hydrocarbon-based solvent and water (preferably, amphiphile is an anionic amphiphile), the mass ratio of the hydrocarbon-based solvent to water is preferably 85:15 to 99.99:0.01, and more preferably 90:10 to 99.9:0.1.

In these preferred embodiments, the solvent may be a mixture of water and an organic solvent. In other preferred embodiments, the solvent may be an acidic aqueous solution such as hydrochloric acid, nitric acid, sulfuric acid, or the like; or a basic aqueous solution such as an aqueous sodium hydroxide solution may be used, in place of or in addition to water, depending on the type of reaction in synthesizing the desired nanosheets.

In the present embodiment, the amphiphilic substance is not particularly limited, but may be an anionic amphiphilic substance. Examples of the anionic amphiphilic substance include a sulfonic acid type surfactant, a sulfate ester type surfactant, a carboxylic acid type surfactant, and a phosphate ester type surfactant.

Examples of the sulfonic acid-type surfactant include an α-sulfofatty acid ester salt such as an α-sulfofatty acid methyl ester salt (CH$_3$(CH$_2$)SCH(SO$_3$Na)COOCH$_3$, wherein s is 8 to 20) such as α-sulfomyristic acid methyl sodium salt or α-sulfostearic acid methyl sodium salt; alkylbenzenesulfonates such as sodium p-toluenesulfonate, sodium cumenesulfonate, sodium octylbenzenesulfonate, and sodium dodecylbenzenesulfonate; alkane sulfonates such as sodium hexylsulfonate, sodium octylsulfonate, sodium decylsulfonate, sodium dodecylsulfonate, sodium tetradecylsulfonate, sodium hexadecylsulfonate, and sodium stearyl sulfonate; α-olefin sulfonate having 8 to 26 carbon atoms.

Examples of the sulfate-type surfactant include R$^1$—OSO$_3$Na (R$^1$=a saturated hydrocarbon group having 8 to 18 carbon atoms or an unsaturated hydrocarbon group having one double bond) such as sodium hexyl sulfate, sodium octyl sulfate, sodium decyl sulfate, sodium dodecyl sulfate, sodium tetradecyl sulfate, sodium hexadecyl sulfate, sodium stearyl sulfate, sodium laureth sulfate, or the like; polyoxyethylene alkyl ether sulfate salts; fatty acid monoglyceride sulfate salts, such as sodium laurate monoglyceride sulfate; fatty acid alkanolamide sulfate salts such as R$^2$CONHCH$_2$CH$_2$OSO$_3$Na (R$^2$=carbon fatty acid having 7 to 20 carbon atoms); and so on.

Examples of the carboxylic acid type surfactant include alkyloyl sarcosines such as sodium octanoate, sodium decanoate, sodium laurate, sodium oleate, sodium myristate, sodium palmitate, sodium stearate, potassium laurate, potassium oleate, perfluorooctanoic acid, perfluorononanoic acid, sodium N-lauroyl sarcosinate, and the like; sodium cocoyl glutamate ((HOOCCH$_2$CH$_2$CH(NHCOR$^3$)COONa), wherein R$^3$ represents an alkyl group having 11 to 17 carbon atoms.).

Examples of the phosphate ester type surfactant include lauryl phosphate; sodium monoalkyl phosphates such as sodium lauryl phosphate, sodium hexyl phosphate, sodium octyl phosphate, sodium decyl phosphate, sodium dodecyl phosphate, sodium tetradecyl phosphate, and sodium hexadecyl phosphate; potassium monoalkylphosphates such as potassium laurylphosphate, potassium hexylphosphate, potassium octylphosphate, potassium decylphosphate, potassium dodecylphosphate, potassium tetradecylphosphate, and potassium hexadecylphosphate; polyoxyethylene alkyl ether phosphoric acid; sodium polyoxyethylene alkyl ether phosphate such as sodium polyoxyethylene lauryl ether phosphate and sodium polyoxyethylene tridecyl ether phosphate. The alkyl group of the anionic amphiphile is preferably 8 to 20 carbon atoms.

Among the above, an alkylbenzenesulfonate is preferable in that it is an ionic surfactant suitable for stabilizing the hyper-swollen lamellar phase, and sodium octylbenzenesulfonate is more preferable in that the onset temperature of the hyper-swollen lamellar phase is more suitable for the reaction temperature.

In the present embodiment, the solvent may also include a surfactant auxiliary for stabilization of the amphiphilic substance. Examples of the surfactant auxiliaries include monohydric alcohols, glycol-based polyhydric alcohols, and derivatives thereof.

Examples of the monohydric alcohol include a monohydric alcohol having 1 to 10 carbon atoms such as ethanol, n-propanol, isopropanol, n-butanol, sec-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2 butanol, neopentyl alcohol, 1-hexanol, 1-heptanol, 1-octanol, 1-nonanol, 1-decanol, 2-methyl-1-pentanol, 4-methyl-2-pentanol, 2-ethyl-1-butanol, 2-heptanol, 3-heptanol, 2-octanol, 2-ethyl-1-hexanol, 3,5,5-trimethyl-1-hexanol; cholesterol and derivatives thereof such as cholesterol, cholesteryl alkenylsuccinate, cholestanol, cholesteryl esters having saturated or unsaturated straight or branched chain hydrocarbon groups having 12 to 36 carbons (preferably 14 to 28 carbons), dehydrocholesterol; and the like.

Examples of the glycol-based polyhydric alcohol or its derivative include glycol ethers such as ethylene glycol monomethyl ether, ethylene glycol monoethyl ether, ethylene glycol monobutyl ether, propylene glycol-1-methyl ether, ethylene glycol diethyl ether, ethylene glycol dimethyl ether, diethylene glycol monomethyl ether, diethylene glycol monoethyl ether, diethylene glycol dimethyl ether, diethylene glycol monobutyl ether, diethylene glycol dimethyl ether, diethylene glycol diethyl ether, triethylene glycol dimethyl ether, or the like; glycol ether acetates such as ethylene glycol methyl ether acetate and diethylene glycol ethyl ether acetate; diols such as ethylene glycol, propylene glycol, 1,3-butylene glycol, diethylene glycol, dipropylene glycol, and hexylene glycol; and polyols such as glycerin, pentaerythritol, sorbitol, and the like.

In the present embodiment, the solvent may be a hydrocarbon-based solvent and water, the amphiphilic substance may be an anionic amphiphilic substance, and the solvent may further include a surfactant auxiliary. In these production methods, when a mixed solvent containing water is used, the content of water is not particularly limited, but in the solvent, the content is preferably 5% by mass or less, more preferably 2.0% by mass or less, and still more preferably 1.5% by mass or less.

In the present embodiment, a known compound usually used as an atomic source of each atom constituting the precursor can be used as a raw material for producing the precursor of the particles of zeolite nanosheet.

The silicon atom source used in the present embodiment is not particularly limited, and may be appropriately selected according to the type of zeolite to be produced. Examples of the silicon atom source include tetraalkoxysilane such as tetramethoxysilane, tetraethoxysilane (TEOS), and the like; tetraalkyl orthosilicate; silica; other silicas such as silica gel, pyrolyzed silica, precipitated silica, colloidal silica, water glass, wet silica, amorphous silica, fumed silica; sodium silicate; kaolinite; diatomaceous earth; aluminum silicate; and the like. Tetraalkoxysilane is preferred in terms of affinity with the organic solvent used as the swelling solvent, and TEOS is more preferred in terms of cost and reaction rate.

The aluminum atom source used in the present embodiment is not particularly limited, and may be appropriately selected according to the type of zeolite to be produced, but may be an aluminum salt such as aluminum chloride, aluminum nitrate, and aluminum sulfate; aluminum alkoxide such as aluminum isopropoxide; aluminate salt; aluminum oxide; aluminum oxyhydroxide; aluminum hydroxide; alumina white; aluminum fluoride; and the like.

In the present embodiment, when the zeolite containing phosphorus (for example, silicoaluminophosphate, aluminophosphate, etc.) is produced, a phosphorus atom source is not particularly limited, and may be appropriately selected depending on the type of the zeolite to be produced, but a phosphorus compound such as phosphoric acid or aluminum phosphate is usually used.

The sheet-like particles of the aluminosilicate according to the present embodiment may contain elements other than silicon and aluminum. When the sheet-like particles of aluminosilicate containing other metal elements are produced, a metal alkoxide of other metal elements may be contained as a raw material of the aluminosilicate.

For example, when the other metal is Fe or Ga, an inorganic acid salt, an organic acid salt, an organometallic compound, or the like having one or both of Fe and Ga is appropriately selected as needed. Examples of the inorganic acid salt include sulfate, nitrate, phosphate, chloride, bromide, and the like; examples of the organic acid salt include acetate, oxalate, citrate, and the like; and examples of the organometallic compound include pentacarbonyl, ferrocene, and the like. Among them, the inorganic acid salts and the organic acid salts are preferable from the viewpoint of solubility in water. In some cases, colloidal oxides or fine powder oxides may be used.

[Specific Example of First Step]

A preferred example of the first step of the producing method of the present embodiment will be described. First, a silicon atom source such as tetraethyl orthosilicate (TEOS) is mixed with water. Sodium hydroxide is further added to the mixture and dissolved. An amphiphilic substance containing 1-pentanol and sodium p-octylbenzenesulfonate (OBS) is then added to the mixture and dissolved. After dissolving the OBS, decane, which is an organic solvent, is added to the mixed solution, and the mixture is stirred at 60° C. for 24 hours. After ethanol is added to the mixed solution after stirring, the resulting precipitate is separated and dried to obtain white powder. The white powder is a mixture of sheet-like particles of amorphous aluminosilicate and OBS.

The resulting sheet-like particles of amorphous aluminosilicate are preferably nanosheets with a thickness of 2 to 100 nm and an aspect ratio (meaning "maximum width/thickness in a particle") of 100 or more.

The thickness and the aspect ratio can be adjusted by appropriately combining conditions such as the thickness of the bilayer, the raw material composition ratio, the reaction temperature, and the reaction time. For example, the aspect ratio can be adjusted by adjusting the reaction time.

In the present embodiment, it is preferable that a plurality of sheet-like particles of aluminosilicate ("Sheet-like particles of aluminosilicate" are sometimes referred to as "aluminosilicate nanosheets.") formed in the super-swelled lamellar phase exist, and the sheet-like particles exist in the super-swelled lamellar phase in a state where they are not substantially agglomerated.

For example, in the specific example of the first step, after adding decane to the mixed solution and stirring at 60° C. for 24 hours, and before adding ethanol to the mixed solution after stirring, it is preferable that the formed sheet-like particles of aluminosilicate are present in the hyper-swollen lamellar phase in a substantially non-agglomerated state. For evaluation of the aggregation state, for example, a dynamic light scattering (DLS) method described later in the embodiment can be used.

Other specific examples will be described in detail.

TEOS and deionized water are mixed in a screw tube. Sodium hydroxide is added to the resulting mixed solution and dissolved. After 1-pentanol is added to the screw tube, OBS is added and dissolved.

Decane is added to the resulting mixed solution, followed by aluminum triisopropoxide. The resulting mixture is stirred with a hot stirrer.

The detailed reaction conditions are shown below.

Decane and 1-pentanol are used as the swelling solvent. An amount of the swelling solvent used is usually 90% by mass or more, preferably 95% by mass or more, and more preferably 98% by mass or more, with respect to the whole system in the formation of the super-swelling lamellar phase. In the embodiment described below, 98% by mass was used.

A content of water is usually 5% by mass or less, preferably 2% by mass or less, and more preferably 1.5% by mass or less. In the embodiment described later, it was 1.1% by mass.

The amount of OBS is usually 3% by mass or less, preferably 2% by mass or less, and more preferably 1% by mass or less. In the embodiment described later, it was 0.95% by mass.

An amount of 1-pentanol is usually 15% by mass or less, preferably 12% by mass or less, and more preferably 10% by mass or less. In the embodiment described later, it was 8.4% by mass.

A Si/Al ratio is typically 1 to 150, preferably 1 to 100, and more preferably 1 to 60. In the embodiment described below, the ratio was 21.

A ratio of NaOH/Al is usually 0 to 20, preferably 0 to 10, and more preferably 0 to 5. In the embodiment described below, the ratio was 4.1.

A reaction temperature is usually 25° C. or more and 90° C. or less, preferably 40° C. or more and 80° C. or less, and more preferably between 60° C. or more and 70° C. or less. In the embodiment described later, the temperature was 64° C.

A stirring speed is usually 0 rpm or more and 1000 rpm or less, preferably 100 rpm or more and 500 rpm or less, and more preferably 200 rpm or more and 300 rpm or less. In the embodiment described later, the speed was 200 rpm.

The reaction time is usually 15 hours or more and 40 hours or less, preferably 18 h or more and 30 hours or less, and more preferably 22 hours or more and 26 hours or less. In the embodiment described later, it was 24 hours.

<Second Step>

In the first step, the sheet-like particles of zeolite are produced by bringing the sheet-like particles of aluminosilicate obtained in the first step into contact with gaseous water in a container using a dry gel conversion (DGC) method. A structure-directing agent may be added to the sheet-like particles of the aluminosilicate. That is, it is preferable that the sheet-like particles of zeolite are produced from the sheet-like particles of aluminosilicate obtained in the first step by contacting with gaseous water in the presence of a structure-directing agent by using a dry gel conversion (DGC) method.

[Structure-Directing Agent]

The structure-directing agent (SDA) may be present in the container when the sheet-like particles of the aluminosilicate are brought into contact with gaseous water.

As the structure-directing agent, amine, imine, or quaternary ammonium salt may be used. Examples of the structure-directing agent include triethylamine, cyclohexylamine, morpholine, piperidine, pyridine, isopropylamine, isobutylamine, N-ethylbutylamine, dipropylamine, N-methylbutylamine, tripropylamine, N,N-diisopropylethylamine, hexamethyleneimine, diisopropylamine, tetraethylammonium hydroxide, N,N,N-trimethyladamantammonium hydroxide (TMAdaOH), tetramethylammonium hydroxide (TMAOH), tetraethylammonium hydroxide (TEAOH), tetrapropylammonium hydroxide (TPAOH), and the like. Among them, triethylamine, cyclohexylamine, morpholine, piperidine, isopropylamine, dipropylamine, N-methylbutylamine, TMAOH, TEAOH, TMAdaOH, TPAOH, or the like are preferable, and triethylamine, morpholine, cyclohexylamine, cyclohexylamine, TMAOH, TEAOH, TMAdaOH, TPAOH, or the like are particularly preferred.

[Dry Gel Conversion (DGC) Method]

In the method for producing the sheet-like particles of zeolite, a solid is obtained by first drying the aluminosilicate sheet-like particles. Thereafter, the obtained solid is brought into contact with gaseous water in a container to produce sheet-like particles of zeolite. In the present invention, the method of bringing the solid into contact with gaseous water is referred to as the dry gel conversion (DGC) method. The sheet-like particles of aluminosilicate may be mixed with a structure-directing agent if necessary.

An order in which the sheet-like particles of aluminosilicate and the structure-directing agent are mixed is not particularly limited, but the structure-directing agent is usually mixed with the sheet-like particles of aluminosilicate. The mixture may be placed in a container with water when performing the DGC method.

When the sheet-like particles of aluminosilicate are mixed with the structure-directing agent, a solvent such as water may be used to enhance dispersibility. In this case, a dry solid is obtained by removing the solvent to such an extent that the mixture retains its shape.

The dry solid may be in powder form, granule form, or a molding having another form; or may be supported on a substrate. Examples of the method for forming the dry solid into granule form include a known granulation method such as an extrusion method, a spray drying method, a stirring granulation method, a rolling granulation method, and the like. The molding having another form includes, for example, molding having honeycomb form, and the molding is usually molded by extrusion molding after adding a binder component or the like as required. Further, examples of a method of forming the dry solid into the form in which the dry solid is supported on the substrate include a method of immersing a honeycomb-like substance made of corrugated paper made of ceramic paper in a gel-like or slurry-like raw material mixture and drying the taken-out honeycomb-like substance.

The dry solid having a predetermined shape (hereinafter referred to as a dry solid molding) may be obtained by molding a gel-like or slurry-like raw material mixture and then drying it, or may be obtained by pulverizing the dry solid once obtained and then molding it. That is, the dry solid molded product may be molded prior to drying or may be molded after crushing the dry solid. The dry solid molding thus obtained is then brought into contact with gaseous water according to the DGC method and crystallized to produce sheet-like particles of zeolite having a predetermined shape.

The dry solid, the liquid water, and the structure-directing agent to be added as necessary are put into a container, and the container is brought into contact with gaseous water under a predetermined pressure, and the temperature in the container is maintained to obtain sheet-like particles of zeolite.

There are no particular restrictions on the method for bringing the dry solid into contact with gaseous water, but there are, for example, a method for holding the dry solid on a stand or on a shelf so that the dry solid is physically separated from the liquid water in a container, and a method for holding the dry solid in a wire net-like container so that the water condensed on the dry solid is quickly removed at the time of raising or lowering the temperature.

The material of the container is not particularly limited, but a container made of stainless steel or a container whose inner surface is coated with stainless steel, titanium, Ni—Cr alloy, Hastelloy, or Teflon (registered trademark) may be used.

As a method for adding the structure-directing agent, a method in which the structure-directing agent is mixed with sheet-like particles of aluminosilicate in advance as described above, or a method in which the structure-directing agent is put in a container together with water when the DGC method is performed, can be used. Among the methods of adding a structure-directing agent, the method of placing the agent in a container together with water in the DGC method is advantageous from the viewpoint of safety because there are few procedures for handling the structure-directing agent that require attention when handling. Other methods of adding structure-directing agents include supplying them as steam separately from water.

The total amount of structure-directing agents affects economy or ease of synthesis of sheet-like particles of zeolite of the desired composition. A molar ratio of the structure-directing agent with respect to the sheet-like particles of aluminosilicate is usually 0.2 or more, preferably 0.5 or more, usually 4 or less, preferably 3 or less, and more preferably 2.5 or less.

The pressure (total pressure) depends on the temperature in the container, and is such that at least a part of the water and the structure-directing agent in the container exist in a gaseous state and the crystallization of the sheet-like particles of zeolite is not inhibited.

An amount of water contained in the container is preferably such that the partial pressure of water is 40% or more of the saturated vapor pressure at the temperature in the container. An amount of 60% or more of the saturated vapor pressure is more preferable, and an amount of 90% or more of the saturated vapor pressure is still more preferable. If the partial pressure of water is less than 40% of the saturated vapor pressure, crystallization may not proceed sufficiently. An amount of water contained in the container is usually 100% to 150% of the amount that gives the saturated vapor pressure of water at the temperature in the container due to the reproducibility of the particle size, the reproducibility of the strength of the molded product, or the economic efficiency. On the other hand, although there is no particular limitation on the upper limit, if the amount of water present in the container is more than 150% of the amount that gives the saturated vapor pressure of water, the amount of energy consumed may be large, which may be economically disadvantageous.

The temperature in the container is set by the ease of synthesis of sheet-like particles of zeolite of a desired composition, but is usually 100° C. or higher, preferably 120° C. or higher, more preferably 130° C. or higher; and usually 220° C. or lower, preferably 200° C. or lower. Lower than the above range, the crystallization rate may be slow; and higher than the above range, impurities may be formed. The temperature inside the container may be constant during synthesis or may be changed stepwise.

The time to maintain the temperature in the container is set by the ease of synthesis of sheet-like particles of zeolite of the desired composition, but is usually 2 hours or more, preferably 3 hours or more, and more preferably 5 hours or more; usually 30 days or less, preferably 10 days or less, and more preferably 4 days or less.

When the sheet-like particles of zeolite are produced in this way, since the separation operation and purification operation are not required because the DGC method is used, the sheet-like particles of zeolite can be easily produced. Since the obtained sheet-like particles of zeolite have high purity, production efficiency is good.

<Third Step>

The producing method of the present embodiment may include a third step of calcining the sheet-like particles of zeolite obtained in the second step, if necessary. Since the sheet-like particles of zeolite obtained in the second step may contain a structure-directing agent, the structure-directing agent contained in the sheet-like particles of zeolite can be removed in the third step.

The sheet-like particles of zeolite produced by the DGC method in the second step may be calcined by a known method depending on the purpose of use. The structure-directing agent is removed from the sheet-like particles of zeolite after calcination, and the sheet-like particles are preferably used as an adsorbent or a catalyst, for example.

The calcination is a process for heat-treating, under a predetermined condition and under the flow of a gas such as air diluted with nitrogen or under reduced pressure, the sheet-like particles of zeolite containing the structure-directing agent (hereinafter referred to as a precursor) which is produced by, for example, the DGC method. As a result, the sheet-like particles of zeolite are obtained by removing a part or the whole of the structure-directing agent in the precursor.

The calcination temperature at which the calcination is carried out is not particularly limited, but the calcination can usually be carried out at a temperature of 400° C. or higher and 600° C. or lower. In this range, the calcination time does not become too long, zeolite having a desired structure can be formed, and the structure-directing agent can be removed. Preferably, calcination is performed at a temperature of 500° C. or higher and 550° C. or lower.

The calcination time is not particularly limited, but it can usually be from 1 hour to 24 hours.

The calcination can be carried out using, for example, a commercially available heating furnace.

The calcination may be carried out in either an air atmosphere or an inert gas atmosphere such as nitrogen, and it is preferable from the viewpoint of cost to carry out the calcination in an air atmosphere.

The obtained precursor may be dried before the calcining step. The drying conditions can be performed under appropriate conditions.

Examples of calcination conditions are shown below.

Calcination temperature: usually 400° C. or higher, preferably 500° C. or higher, usually 600° C. or lower
Temperature rise/cooling rate: 5 to 10° C./min
Calcination atmosphere: air
Calcination pressure: atmospheric pressure
Calcination time: 5 to 10 hours By using the producing method of the present embodiment, sheet-like particles of zeolite having various crystal structures can be produced by adjusting the Si/Al ratio, the type of structure-directing agent, the processing conditions of the second step, and the like. Further, by using the producing method of the present embodiment, it is possible to manufacture nano-sized sheet-like particles having a thickness of 1 nm to 100 nm and a ratio (aspect ratio) of the maximum width to the thickness of 20 or more (referred to as "nanosheet" in the present invention). In the present embodiment, the nanosheet-like particles of zeolite (referred to as "zeolite nanosheet" in the present invention) preferably have a thickness of 1 nm to 100 nm, and a ratio (aspect ratio) of the maximum width to the thickness of 50 or more; more preferably have a thickness of 1 nm to 50 nm, a ratio (aspect ratio) of the maximum width to the thickness of 100 or more; still more preferably have a thickness of 1 nm to 20 nm, and a ratio (aspect ratio) of the maximum width to the thickness of 200 or more.

<Sheet-Like Particles of Zeolite Having Various Crystal Structures and Method for Producing the Same>

Zeolite nanosheets having various crystal structures will be described below as specific examples of sheet-like particles of zeolite produced by the method of the present embodiment.

<Crystal Structure of Sheet-Like Particles of Zeolite>

The crystal structures of zeolites are classified by the International Zeolite Association (IZA) using a structural code using three letters. In the present specification, zeolites having respective crystal structures are sometimes expressed by using the structural codes. Specifically, when the structural code of the zeolite is CHA, the zeolite is expressed as "CHA-type zeolite".

There is also a classification method based on the size of the pore size of zeolite. In this case, it is classified by the number of oxygen atoms contained in the ring structure (8-membered ring, 10-membered ring, 12-membered ring, etc.) as follows. In the case of zeolite having pores having a plurality of sizes, the zeolite is represented by the largest pore. (I) Zeolite with Small-Pore and 8-Membered Oxygen Ring Structure (meaning "small pore zeolite" in the present invention)

Examples of zeolite species (structural codes) include ANA, CHA, ERI, GIS, KFI, LTA, NAT, PAU, PHI, SOD, YUG, DDR, and the like.

(II) Zeolite with Medium-Pore and 10-Membered Oxygen Ring Structure (referred to as "medium pore zeolite" in the present invention)

Examples of zeolite species (structural codes) include AEL, EUO, FER, HEU, MEL, MFI, NES, TON, WEI, and the like.

(III) Zeolite with Large-Pore and 12-Membered Oxygen Ring Structure (meaning "large pore zeolite" in the present invention)

Examples of zeolite species (structural codes) include AFI, ATO, BEA, CON, FAU, GME, LTL, MOR, MTW, OFF, and the like.

As described above, the zeolite nanosheet of the present embodiment is a two-dimensional crystal with limited crystal growth in a thickness direction. The zeolite nanosheet of the present embodiment preferably includes a small-pore zeolite nanosheet, a medium-pore zeolite nanosheet, a large-pore zeolite nanosheet, or the like.

Examples of the small-pore zeolite nanosheets of the present embodiment include ANA-type zeolite nanosheets, CHA-type zeolite nanosheets, ERI-type zeolite nanosheets, GIS-type zeolite nanosheets, KFI-type zeolite nanosheets, LTA-type zeolite nanosheets, NAT-type zeolite nanosheets, PAU-type zeolite nanosheets, PHI-type zeolite nanosheets, SOD-type zeolite nanosheets, YUG-type zeolite nanosheets, and DDR-type zeolite nanosheets. Among them, the CHA-type zeolite nanosheets, the PHI-type zeolite nanosheets, and the SOD-type zeolite nanosheets will be described in detail in Examples.

Examples of the medium-pore zeolite nanosheets in the present embodiment include AEL-type zeolite nanosheets, EUO-type zeolite nanosheets, FER-type zeolite nanosheets, HEU-type zeolite nanosheets, MEL-type zeolite nanosheets, MFI-type zeolite nanosheets, NES-type zeolite nanosheets, TON-type zeolite nanosheets, WEI-type zeolite nanosheets, and the like. Among them, the MFI-type zeolite nanosheets will be described in detail in Examples.

Examples of the large-pore zeolite nanosheets of the present embodiment include AFI-type zeolite nanosheets, ATO-type zeolite nanosheets, BEA-type zeolite nanosheets, CON-type zeolite nanosheets, FAU-type zeolite nanosheets, GME-type zeolite nanosheets, LTL-type zeolite nanosheets, MOR-type zeolite nanosheets, MTW-type zeolite nanosheets, OFF-type zeolite nanosheets, and the like.

The sheet-like particles of zeolite according to the present embodiment include, but are not limited to, aluminosilicate, silicoaluminophosphate, aluminophosphate, and those in which a part of these zeolites is replaced with another metal species (e.g., metalloaluminosilicate, metalloaluminophosphate, etc.), and are preferably aluminosilicate. In the present case, a mass ratio of $Al_2O_3$ to $SiO_2$ of all of the sheet-like particles of zeolite, although not particularly limited, is preferably 0.1 to 30, more preferably 0.15 to 20, and still more preferably 0.2 to 15.

Further, the sheet-like particles of the zeolite of the present invention may contain, other than components constituting the skeleton structure, "those having cation species capable of ion exchange with other cations". The cations in such a case include protons; alkali elements such as Li, Na, and K; alkaline earth elements such as Ca; and rare earth elements such as La and Ce; and the like. Among them, protons, alkali elements, and alkaline earth elements are preferable.

The zeolite nanosheets of the present embodiment can be produced by optimizing the Si/Al molar ratio, the structure-directing agent, and the treatment condition by using the method for producing the sheet-like particles of zeolite. Specific examples of the method for producing zeolite nanosheets of various crystal structures are shown in Table 1.

TABLE 1

| Zeolite nanosheets having various crystal structures | First step conditions Amphiphilic substance Solvent Si source and Al source Si/Al molar ratio Processing temperature and processing time | Second step conditions Structure-directing agents; processing temperature and processing time |
|---|---|---|
| PHI type | 1-Pentanol and OBS<br>Decane<br>TEOS and aluminum triisopropoxide<br>Si/Al molar ratio 5 to 150<br>60° C., 24 hours | TMAdaOH<br>160° C., 2 days |
| SOD type | 1-Pentanol and OBS<br>Decane<br>TEOS and aluminum triisopropoxide<br>Si/Al molar ratio 1 to 50<br>60° C., 24 hours | Sodium hydroxide<br>160° C., 2 days |
| CHA type | 1-Pentanol and OBS<br>Decane<br>TEOS and aluminum triisopropoxide<br>Si/Al molar ratio 5 to 150<br>60° C., 24 hours | TMAdaOH<br>160° C., 4 days |
| BEA type | 1-Pentanol and OBS<br>Decane<br>TEOS and aluminum triisopropoxide<br>Si/Al molar ratio 5 to 150<br>60° C., 24 hours | TEAOH<br>120° C., 3 days |
| CAN type | 1-Pentanol and OBS<br>Decane<br>TEOS and aluminum triisopropoxide<br>Si/Al molar ratio 2 to 8<br>60° C., 24 hours | TMAOH<br>180° C., 2 days |
| ANA type | 1-Pentanol and OBS<br>Decane<br>TEOS and aluminum triisopropoxide<br>Si/Al molar ratio 4 to 16<br>60° C., 24 hours | TMAOH<br>180° C., 2 days |
| MOR type | 1-Pentanol and OBS<br>Decane<br>TEOS and aluminum triisopropoxide<br>Si/Al molar ratio 16 to 32<br>60° C., 24 hours | TMAOH<br>180° C., 2 days |
| MFI type | 1-Pentanol and OBS<br>Decane<br>TEOS and aluminum triisopropoxide<br>Si/Al molar ratio 5 to 150<br>60° C., 24 hours | TPAOH<br>160° C., 2 days |

TEOS: tetraethyl orthosilicate
OBS: sodium p-octylbenzenesulfonate
TMAdaOH: N,N,N-trimethyladamantammonium hydroxide
TPAOH: tetrapropylammonium hydroxide
TMAOH: tetramethylammonium hydroxide
TEAOH: tetraethylammonium hydroxide TEOS: tetraethyl orthosilicate
OBS: sodium p-octylbenzenesulfonate
TMAdaOH: N,N,N-trimethyladamantammonium hydroxide
TPAOH: tetrapropylammonium hydroxide
TMAOH: tetramethylammonium hydroxide
TEAOH: tetraethylammonium hydroxide

[Specific Examples of the Second Step and the Third Step]

A preferred example of the first step of the producing method of the present embodiment will be described.

<Nanosheet of SOD-Type Zeolite>

A dry gel is obtained by adding NaOH to the white powder, mixing it thoroughly, and drying it at 90° C. for 1 night. The obtained dry gel is crystallized by a dry gel conversion method using an autoclave. The detailed reaction conditions are shown below. The product is washed with deionized water and dried at 90° C. overnight.

A ratio of NaOH/aluminosilicate was usually 0 to 1, preferably 0 to 0.5, more preferably 0 to 0.3, and in the Examples described below, 0.3.

A crystallization temperature was usually 100° C. to 220° C., preferably 120° C. to 200° C., more preferably 160° C. to 180° C., and in the Example described below, 180° C.

A crystallization time was usually 2 hours to 30 days, preferably 3 hours to 10 days, more preferably 5 hours to 4 days, and in the Example described below, 48 hours.

<Nanosheet of MFI-Type Zeolite>

A dry gel is obtained by adding TPAOH to the white powder, mixing it thoroughly, and drying it at 90° C. for 1 night. The obtained dry gel is crystallized by a dry gel conversion method using an autoclave. The detailed reaction conditions are shown below. The product is washed with deionized water and dried at 90° C. overnight. The obtained sample is calcined.

A ratio of TPAOH/aluminosilicate was usually 0.5 to 10, preferably 1 to 5, more preferably 2 to 4, and in the Example described below, 3.

A crystallization temperature was usually 100° C. to 220° C., preferably 120° C. to 200° C., more preferably 160° C. to 180° C., and in the Example described below, 180° C.

A crystallization time was usually 2 hours to 30 days, preferably 3 hours to 10 days, more preferably 5 hours to 4 days, and in the Example described below, 48 hours.

A calcination temperature was typically 400° C. to 600° C., preferably 500° C. to 600° C., more preferably 550° C. to 600° C., and in the Example described below, 550° C.

A calcination time was usually 2 to 24 hours, preferably 3 to 15 hours, more preferably 5 to 10 hours, and in the Example described below, 5 hours.

<Nanosheet of PHI-Type Zeolite>

A dry gel is obtained by adding TMAdaOH to the white powder, mixing it thoroughly, and drying it at 90° C. for 1 night. The obtained dry gel is crystallized by a dry gel conversion method using an autoclave. The product is washed with deionized water and dried at 90° C. overnight. The obtained sample is calcined.

A ratio of TMAdaOH/aluminosilicate was usually 0.5 to 20, preferably 1 to 15, more preferably 5 to 10, and in the examples described below, 7.

A crystallization temperature was usually 100° C. to 220° C., preferably 120° C. to 200° C., more preferably 160° C. to 180° C., and in the Example described below, 160° C.

A crystallization time was usually 2 hours to 30 days, preferably 3 hours to 10 days, more preferably 5 hours to 4 days, and in the Example described below, 48 hours.

A calcination temperature was typically 400° C. to 600° C., preferably 500° C. to 600° C., more preferably 550° C. to 600° C., and in the Example described below, 550° C.

A calcination time was usually 2 to 24 hours, preferably 3 to 15 hours, more preferably 5 to 10 hours, and in the Example described below, 5 hours.

<Nanosheet of CHA-Type Zeolite Nanosheet>

A dry gel is obtained by adding TMAdaOH to the white powder, mixing it thoroughly, and drying it at 90° C. for 1 night. The obtained dry gel is crystallized by a dry gel conversion method using an autoclave. The product is washed with deionized water and dried at 90° C. overnight. The obtained sample is calcined.

A ratio of TMAdaOH/aluminosilicate was usually 0.5 to 20, preferably 1 to 15, more preferably 5 to 10, and in the Examples described below, 7.

A crystallization temperature was typically 100° C. to 220° C., preferably 120° C. to 200° C., more preferably 160° C. to 190° C., and in the Example described below, 160° C.

A crystallization time was usually 2 hours to 30 days, preferably 3 hours to 10 days, more preferably 5 hours to 4 days, and in the Example described below, 96 hours.

A calcination temperature was typically 400° C. to 600° C., preferably 500° C. to 600° C., more preferably 550° C. to 600° C., and in the Example described below, 550° C.

A calcination time was usually 2 to 24 hours, preferably 3 to 15 hours, more preferably 5 to 10 hours, and in the Example described below, 5 hours.

<Catalyst Composition for Membrane Reactor>

The zeolite nanosheets of the present invention (particles of zeolite nanosheet) can be used as a catalyst composition for a membrane reactor.

For example, by forming a zeolite film by using the zeolite nanosheets of the present invention, the zeolite film which is thinner than the zeolite film formed by using the zeolite of bulk sample (it is also called "zeolite bulk" or "bulk zeolite". For example, crystals are grown in a three-dimensional direction and are synthesized by a conventional method. Specific examples include a bulk sample of zeolite synthesized in a Comparative Synthesis Example described later.) can be obtained. Therefore, since a thickness of the zeolite film is reduced, the permeation rate of the product is further improved.

In the zeolite film produced by using the zeolite nanosheets of the present invention, molecules larger than the pores of zeolite are decomposed on a surface of the zeolite sheets of the present invention, and only the product smaller than the pores can be recovered.

<Catalytic Additive for Cracking Waste Plastics and Recycling Method for Waste Plastics>

The zeolite nanosheets of the present invention (particles of zeolite nanosheets) can be used as a catalyst additive for cracking waste plastics.

For example, the waste plastic can be efficiently decomposed by adding the zeolite nanosheets to the waste plastic (for example, addition of 0.1 to 100 parts by mass of the zeolite nanosheets of the present invention with respect to 100 parts by mass of the waste plastic) and heating it. The heavy light oil produced from the waste plastic can be reused as fuel.

The catalyst additive for cracking the waste plastics containing the zeolite nanosheets of the present invention can advance the cracking reaction more efficiently than a catalyst containing zeolite of an ordinary bulk sample. This is because the surface area of the sample of zeolite nanosheets is larger than that of the bulk sample of zeolite, so that the cracking reaction can proceed more efficiently.

Further, for example, decomposition at a low heating temperature and decomposition that decomposition product becomes olefin enrichment can be expected.

A method for recycling plastic of the present invention is not particularly limited, but includes, for example, a step of mixing waste plastic with the sheet-like particles of zeolite of the present invention as a reaction-activation component; a step of thermally decomposing the mixture obtained in the mixing step; and the like. The sheet-like particles of zeolite of the present invention as the reaction-activation component may be a catalyst additive for cracking the waste plastic. In the mixing step, it is preferable to add 0.1 to 100 parts by mass of the zeolite nanosheets of the present invention with respect to 100 parts by mass of the waste plastic.

Although the preferred embodiment of the present invention has been described in detail above, the present invention is not limited to a specific embodiment, and various modifications and variations are possible within the scope of the gist of the present invention described in the claims.

EXAMPLE

The present invention will be described below in more detail by using Examples and Comparative Examples, but the present invention is not limited to the following Examples.

(Evaluation of Zeolite Nanosheet)
<AFM Measurement>
Atomic force microscope (AFM): MMAFM-2, manufactured by Veeco Instruments
<SEM Measurement>
Scanning electron microscope (SEM): JED-2300 Analysis Station Plus manufactured by JEOL Co., Ltd.
Acceleration voltage: 15 kV
<TEM Measurement>
Transmission electron microscope (TEM): JSM-6700 F manufactured by JEOL Co., Ltd.
<X-Ray Diffraction Spectrum Measurement>
X-ray diffractometer (XRD): Panarytical X'Pert PRO
X-Ray source: CuKα
Bulb voltage: 45 kV
Bulb current: 40 mA
Range of measurement: 5 to 45°
<EDX Measurement>
A Si/Al molar ratio on the nanosheet surface was measured by elemental analysis using energy dispersive X-ray spectroscopy (EDX).

Comparative Synthesis Example 1

<Synthesis of Zeolite (CHA Type) of Bulk Sample>
Sodium hydroxide (manufactured by Wako Pure Chemical Industries, Ltd., 0.4 g) and N,N,N-trimethyladamantammonium hydroxide (TMAdaOH: 8.62 g, manufactured by Sachem Co., Ltd.) were added to deionized water (28.6 g) to obtain a mixture. Then, colloidal silica (8.0 g) and aluminum hydroxide (0.366 g) were added to the resulting mixture, and the mixture was stirred using a stirrer at room temperature at 300 rpm for 5 hours. The resulting solution was then placed in a cylindrical container (made of Teflon (Registered Trade Mark): 8 cm in diameter and 4 cm in height). Then, this material was put into an autoclave and sealed, and then held at 160° C. for 4 days in an oven of the autoclave to perform hydrothermal synthesis. Thereafter, the container was taken out of the oven of the autoclave and was allowed to cool at room temperature. The product thus obtained in the container was washed with deionized water, and then the washed product was dried at 90° C. for 16 hours to obtain a solid. Zeolite (CHA type) of a bulk sample was synthesized by calcining the solid thus obtained at 550° C. for 5 hours in air.

Example 1

(Production of Aluminosilicate Nanosheets)
Tetraethyl orthosilicate ("TEOS": Wako Pure Chemical Industries, Ltd., 74 mg) and deionized water (320 mg) were mixed in a screw tube, and further sodium hydroxide (manufactured by Wako Pure Chemical Industries, Ltd., 3 mg) was added and dissolved to give a mixed solution. Next, 1-pentanol (manufactured by Wako Pure Chemical Industries, Ltd. 2.5 g) and sodium p-octylbenzenesulfonate (OBS: Wako Pure Chemical Industries, Ltd., 280 mg) were added to the resulting mixed solution, and then OBS was dissolved by ultrasonic stirring. Decane (26.6 g) and aluminum triisopropoxide (manufactured by Nacalai Tesque, INC., 3.5 mg) were added to the mixed solution obtained by dissolving OBS, and the resulting mixed solution was stirred at 60° C. at 200 rpm for 24 hours using a hot stirrer. A white precipitate was precipitated by adding ethanol to the mixed solution after stirring, and the precipitate was recovered by centrifugation (11000 rpm, 1 hour). The recovered precipitate was dried at 90° C. for 16 hours to obtain a white powder.

As a result of XRD measurement of the obtained white powder, it showed a peak similar to that of OBS. Next, the white powder was washed with methanol, and the resulting washed product was subjected to XRD measurement, which indicated that it was an amorphous aluminosilicate. The white solid obtained was found to be a mixture of aluminosilicate nanosheets and OBS.

Figure 1:
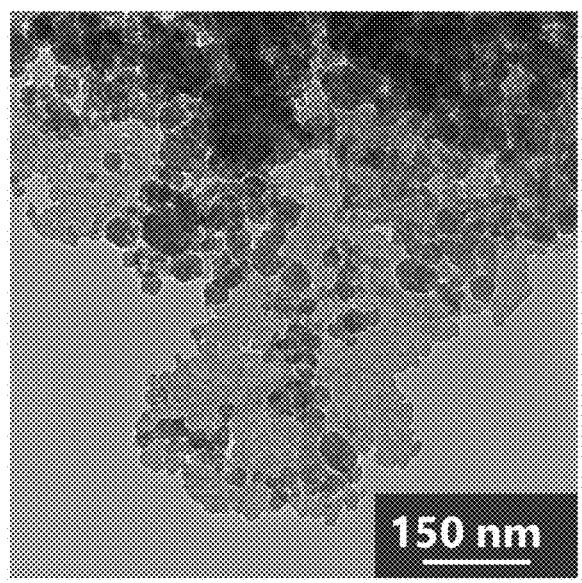
FIG. 1 is a TEM image of a mixture of aluminosilicate nanosheets and OBS obtained in Example 1.
Figure 2:
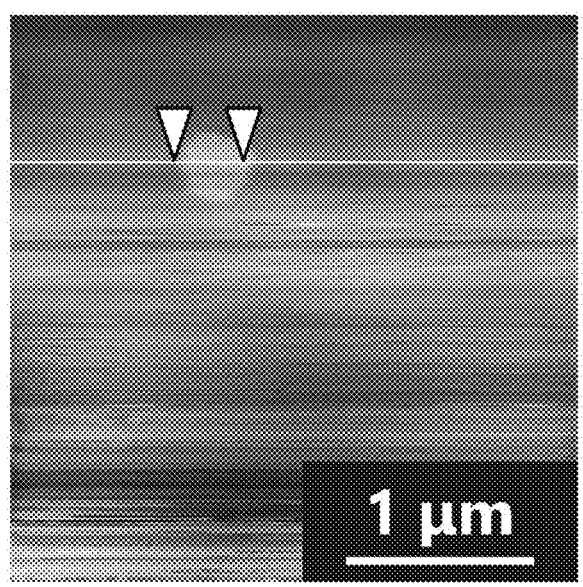
FIG. 2 is AFM data of a mixture of aluminosilicate nanosheets and OBS obtained in Example 1.
Figure 3:
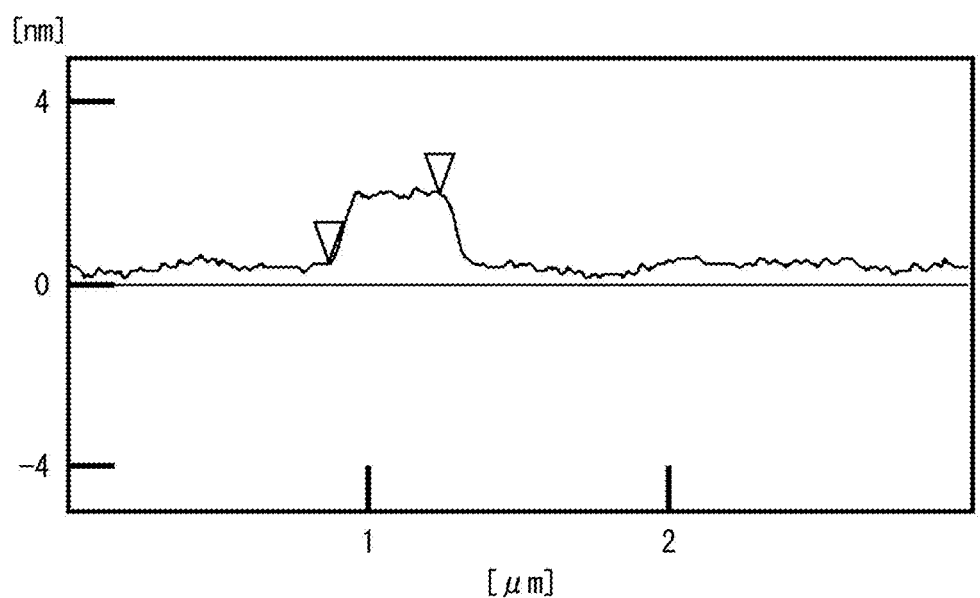
FIG. 3 is AFM data of a mixture of aluminosilicate nanosheets and OBS obtained in Example 1.

The measured results of AFM and TEM are shown in FIGS. 1 to 3.

From the AFM measurement results, the thickness was 1.5 nm and the aspect ratio was 250.

Example 2

(Production of CHA-Type Zeolite Nanosheet)
The white powder containing aluminosilicate nanosheets obtained in Example 1 was mixed with N,N,N-trimethyladamantammonium hydroxide (TMAdaOH: 1.4 g, manufactured by Sachem Co., Ltd.), and the resulting mixture was dried at 90° C. for 16 hours to obtain 650 mg of a dry gel.

The resulting dry gel was placed in a cylindrical container (made of Teflon (Registered Trade Mark): diameter 4 cm, height 2.5 cm). The cylindrical container was then placed in another cylindrical container (made of Teflon (Registered Trade Mark): 8 cm in diameter and 4 cm in height) containing deionized water (5 g). These were placed in an autoclave and sealed, and then held at 160° C. for 4 days in an oven of the autoclave to perform dry gel conversion. Thereafter, the container was taken out of the oven of the autoclave and was allowed to cool at room temperature. The product thus obtained in the container was washed with deionized water, and then the washed product was dried at 90° C. for 16 hours to obtain a solid.

Figure 4:
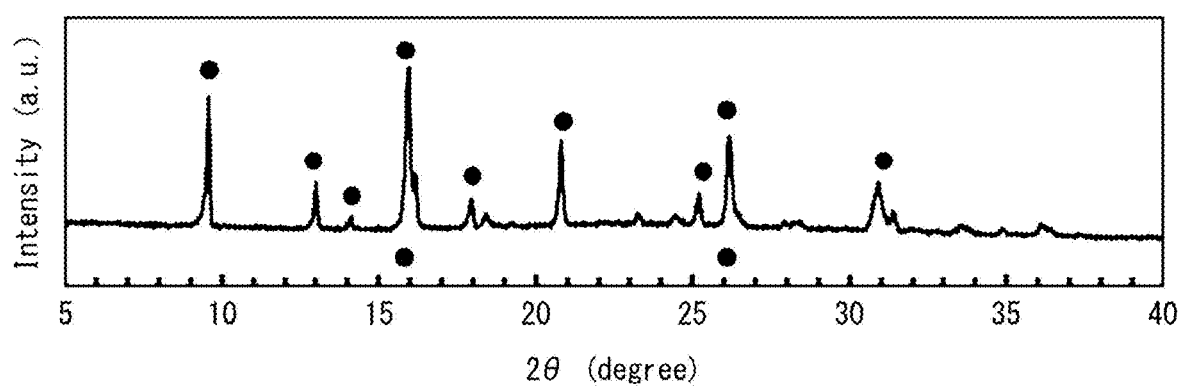
FIG. 4 is XRD data of a CHA-type zeolite nanosheet obtained in Example 2.

The solid thus obtained was calcined at 550° C. for 10 hours in air. Next, the obtained calcined product was subjected to XRD measurement, and it was found that the solid had a CHA-type structure (FIG. 4).

Figure 5:
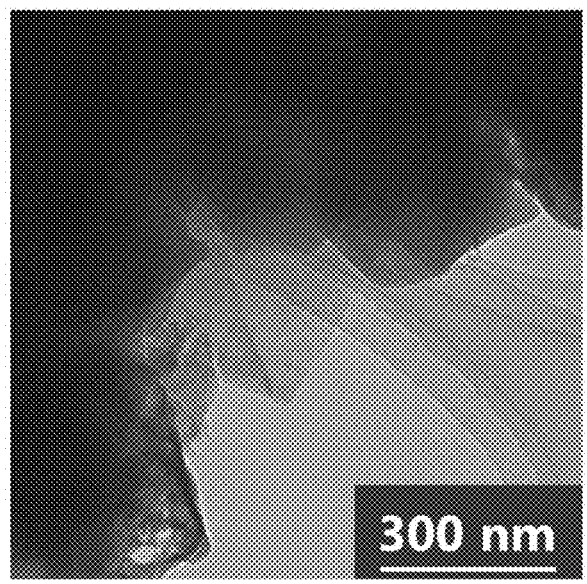
FIG. 5 is a TEM image of a CHA-type zeolite nanosheet obtained in Example 2.
Figure 6:
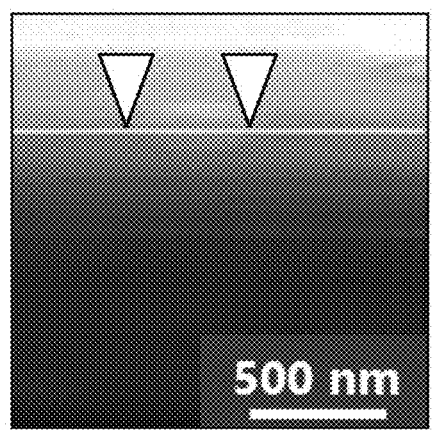
FIG. 6 is AFM data of a CHA-type zeolite nanosheet obtained in Example 2.
Figure 7:
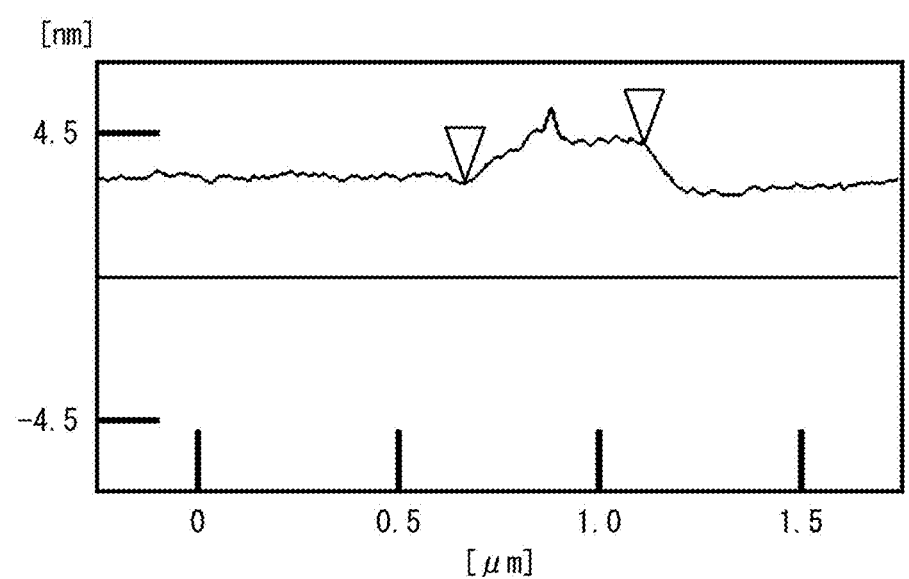
FIG. 7 is AFM data of a CHA-type zeolite nanosheet obtained in Example 2.
Figure 8E:
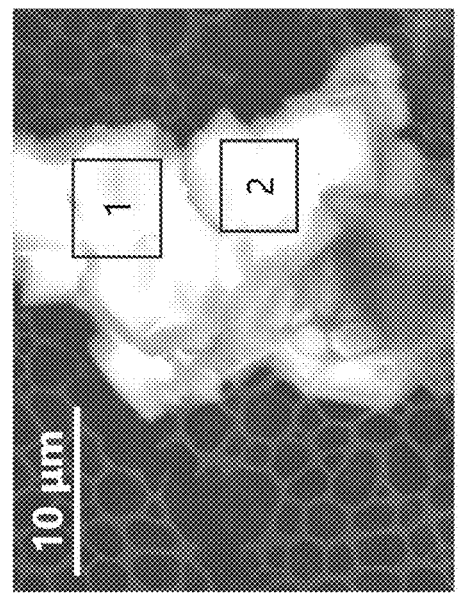
FIG. 8E is an SEM image of a CHA-type zeolite nanosheet obtained in Example 2.
Figure 8B:
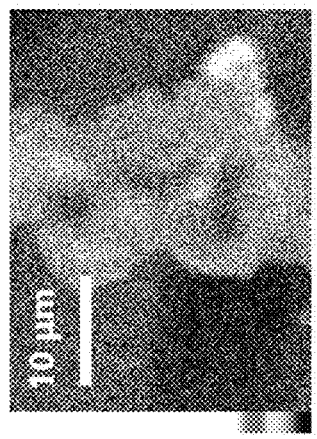
FIG. 8B is an EDX image (Na) of a CHA-type zeolite nanosheet obtained in Example 2.
Figure 8D:
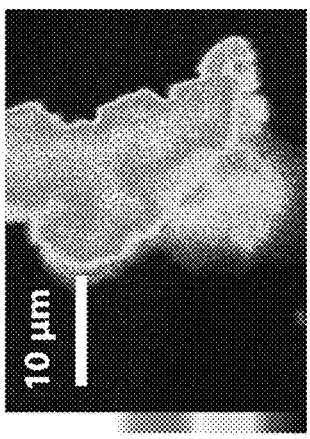
FIG. 8D is an EDX image (Si) of a CHA-type zeolite nanosheet obtained in Example 2.
Figure 8A:
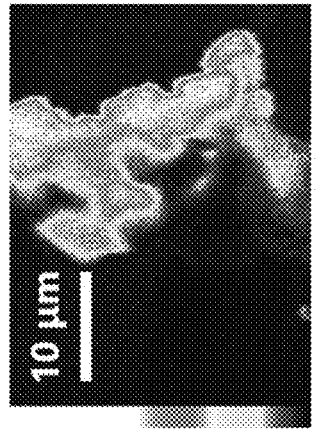
FIG. 8A is an EDX image (O) of a CHA-type zeolite nanosheet obtained in Example 2.
Figure 8C:
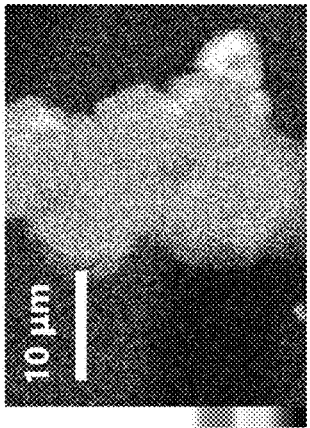
FIG. 8C is an EDX image (Al) of a CHA-type zeolite nanosheet obtained in Example 2.

The measured results of AFM and TEM are shown in FIGS. 5 to 7. From the AFM measurement result of this solid, the thickness is 1.4 nm. The aspect ratio was 860.

The measurement results of EDX and SEM are shown in FIGS. 8A-8E. From the results of EDX of the solid, the molar ratio of Si/Al at the first site is 17.65/1.86 and the molar ratio of Si/Al at the first site is 23.75/2.90. From the average value, the molar ratio of Si/Al was 8.8.

Example 3

(Production of PHI Zeolite Nanosheet)

Figure 9:
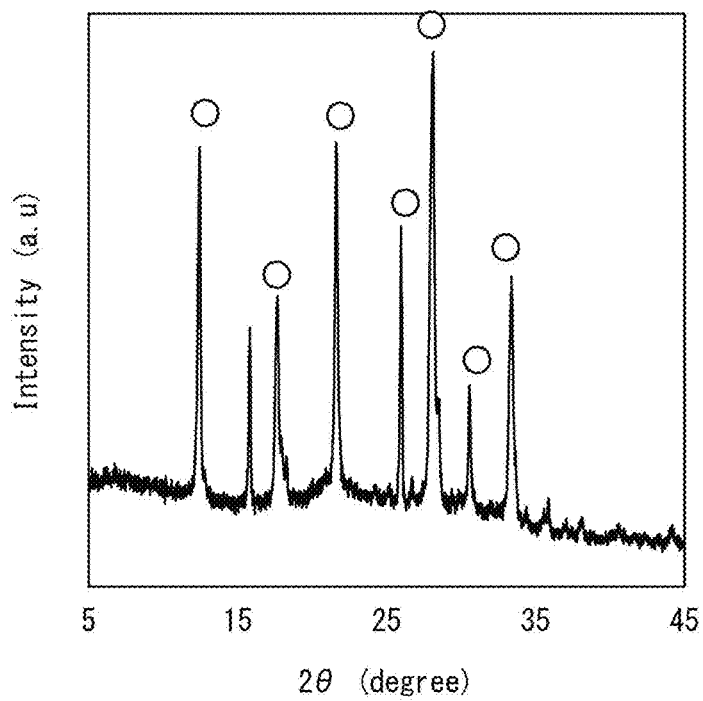
FIG. 9 is XRD data of a PHI-type zeolite nanosheet obtained in Example 3.

A solid was obtained by the same method as in Example 2 except that the time for dry gel conversion was changed to 2 days. As a result of XRD measurement of the calcined product of the obtained solid (FIG. 9), it was found that the solid had a PHI-type structure.

Figure 10:
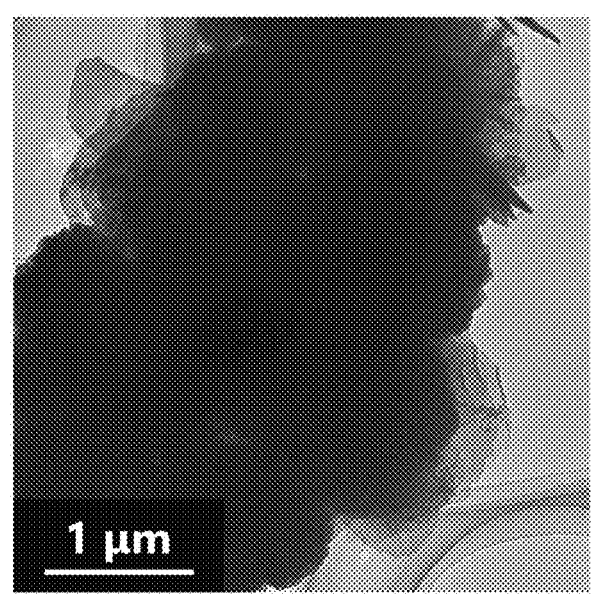
FIG. 10 is a TEM image of a PHI zeolite nanosheet obtained in Example 3.

The TEM measurement results are shown in FIG. 10.

From the AFM measurement result of the solid, the thickness was 1.3 nm and the aspect ratio was 150.

Example 4

(Production of MFI-Type Zeolite Nanosheet)

A dry gel was obtained by the same manner as in Example 2 except that tetrapropylammonium hydroxide ("TPAOH": 1.2 g, manufactured by Tokyo Kasei Co., Ltd.) was used instead of TPAdaOH in Example 2.

Dry gel conversion was performed using the obtained dry gel in the same manner as in Example 2 except that the reaction time was set to 2 days.

The obtained solid was calcined at 550° C. for 5 hours to obtain an MFI-type zeolite nanosheet.

Figure 11:
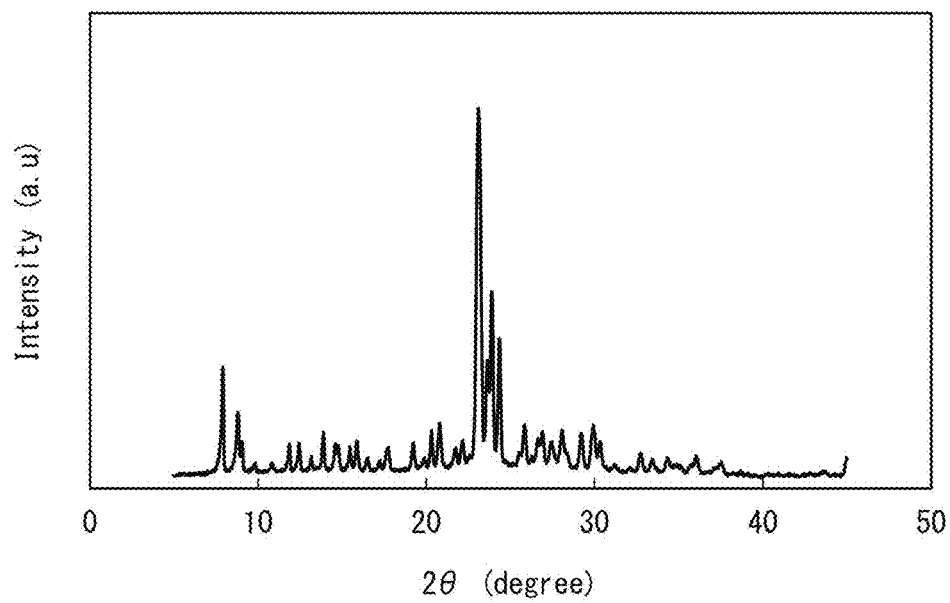
FIG. 11 is XRD data of an MFI-type zeolite nanosheet obtained in Example 4.
Figure 12:
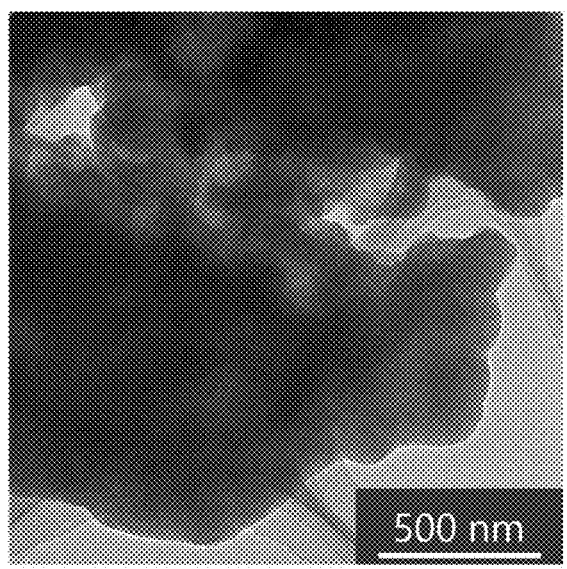
FIG. 12 is a TEM image of an MFI-type zeolite nanosheet obtained in Example 4.
Figure 13:
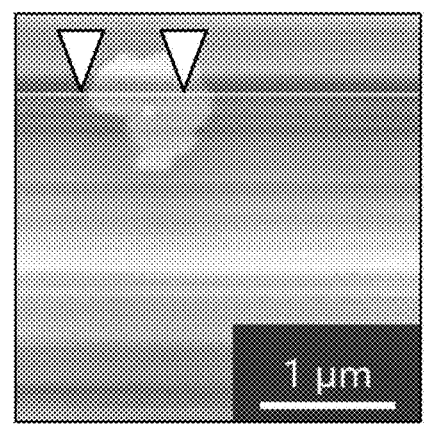
FIG. 13 is AFM data of an MFI-type zeolite nanosheet obtained in Example 4.
Figure 14:
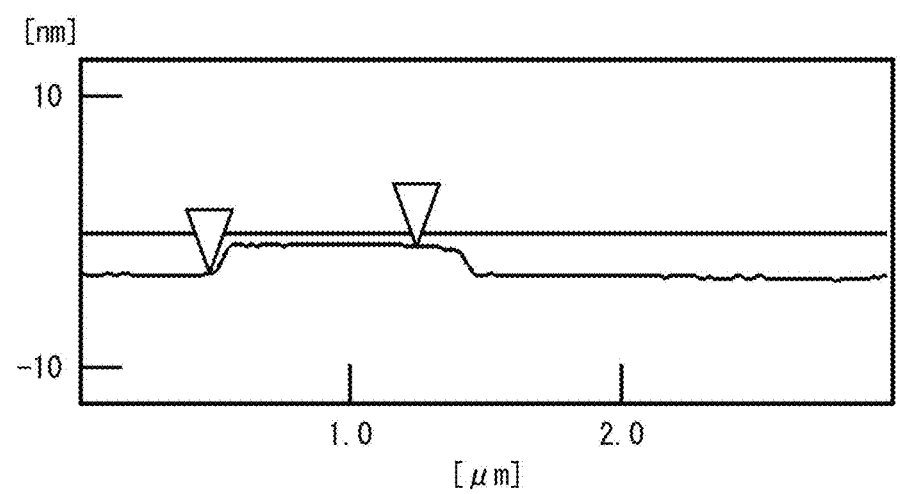
FIG. 14 is AFM data of an MFI-type zeolite nanosheet obtained in Example 4.

The measurement results of XRD are shown in FIG. 11.
The TEM measurement results are shown in FIG. 12.
The AFM measurement results are shown in FIGS. 13 and 14. AFM results indicate that the nanosheet has a thickness of 2 nm. The aspect ratio was 500.

In the method for producing the MFI-type zeolite nanosheet disclosed in Patent Document 2, a special organic surfactant was used. The organic surfactant simultaneously has two functions of a structure-directing agent and a surfactant. In the producing method of the present invention, an optimized amphiphilic substance and a structure-directing agent were separately used for each step in a formation step and a zeolite crystallization step for producing an aluminosilicate nanosheet. Therefore, more kinds of zeolite nanosheets can be produced by the present method than by the production method of Patent Document 2.

Example 5

(Production of SOD-Type Zeolite Nanosheet)

In Example 1, a white powder containing an aluminosilicate nanosheet was obtained by the same method as in Example 1 except that sodium hydroxide was not used.

A dry gel was obtained by the same manner as in Example 2 except that 2.8 mg of sodium hydroxide was used in place of TPAdaOH in Example 2 for the white powder.

Dry gel conversion was performed using the obtained dry gel in the same manner as in Example 2 except that the reaction time was set to 2 days.

The resulting solid was washed with deionized water, and the resulting wash was dried at 90° C. for 16 hours. From the result of XRD measurement, it was found that the solid had an SOD-type structure. The thickness was 1.4 nm and the aspect ratio was 130.

Figure 15:
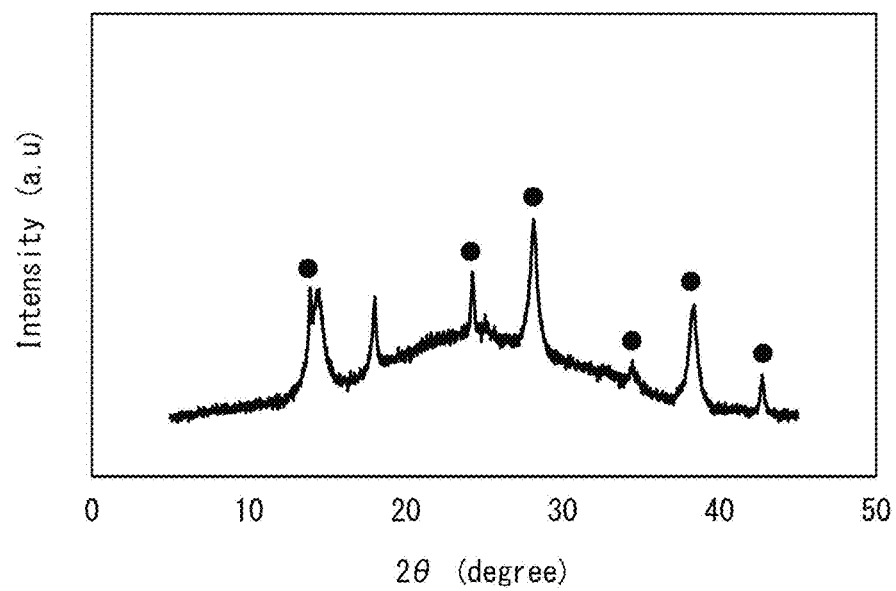
FIG. 15 is XRD data of an SOD-type zeolite nanosheet obtained in Example 5.
Figure 16:
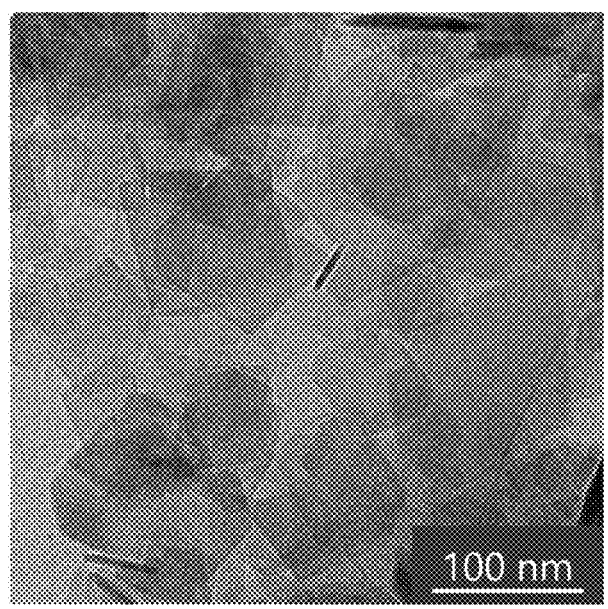
FIG. 16 is a TEM image of an SOD-type zeolite nanosheet obtained in Example 5.

The result of the XRD measurement is shown in FIG. 15.
The result of the TEM measurement is shown in FIG. 16.

Example 6

(Nanosheet of SOD-Type Zeolite)

A dry gel was obtained by adding NaOH to the white powder, mixing it thoroughly, and drying it at 90° C. for 1 night. The obtained dry gel was crystallized by a dry gel conversion method using an autoclave. The detailed reaction conditions are shown below. The product was washed with deionized water and dried at 90° C. overnight.

NaOH/aluminosilicate ratio: 0.3
Crystallization temperature: 180° C.
Crystallization time: 48 hours Example 7

(Nanosheet of MFI-Type Zeolite)

A dry gel was obtained by adding TPAOH to the white powder, mixing it thoroughly, and drying it at 90° C. for 1 night. The obtained dry gel was crystallized by a dry gel conversion method using an autoclave. The detailed reaction conditions are shown below. The product was washed with deionized water and dried at 90° C. overnight. The obtained sample was calcined.

TPAOH/Alumino silicate: 2
Crystallization temperature: 180° C.
Crystallization time: 48 hours
Calcination temperature: 550° C.
Calcination time: 5 hours Example 8

(Nanosheet of PHI-Type Zeolite)

A dry gel was obtained by adding TMAdaOH to the white powder, mixing it thoroughly, and drying it at 90° C. overnight to obtain a dry gel. The obtained dry gel was crystallized by a dry gel conversion method using an autoclave. The product was washed with deionized water and dried at 90° C. overnight. The obtained sample was calcined.

TMAdaOH/Aluminosilicate: 7
Crystallization temperature: 160° C.
Crystallization time: 48 hours
Calcination temperature: 550° C.
Calcination time: 5 hours Example 9

<Nanosheet of CHA-Type Zeolite Nanosheet>

A dry gel was obtained by adding TMAdaOH to the white powder, mixing it thoroughly, and drying it at 90° C. overnight. The obtained dry gel was crystallized by a dry gel conversion method using an autoclave. The product was washed with deionized water and dried at 90° C. overnight. The obtained sample was calcined.

TMAdaOH/Aluminosilicate: 7
Crystallization temperature: 160° C.
Crystallization time: 96 hours
Calcination temperature: 550° C.
Calcination time: 5 hours

Example 10

<Evaluation of Aggregation State of Aluminosilicate Nanosheets in Hyper-Swollen Lamellar Phase>

In Example 1, a solution after synthesis of aluminosilicate (in the hyper-swollen lamellar phase) obtained by stirring at 60° C. and 200 rpm for 24 hours was used as it was, and the aggregated state was evaluated by a dynamic light scattering (DLS) method described below. The results are shown in FIG. 17.

Figure 17:
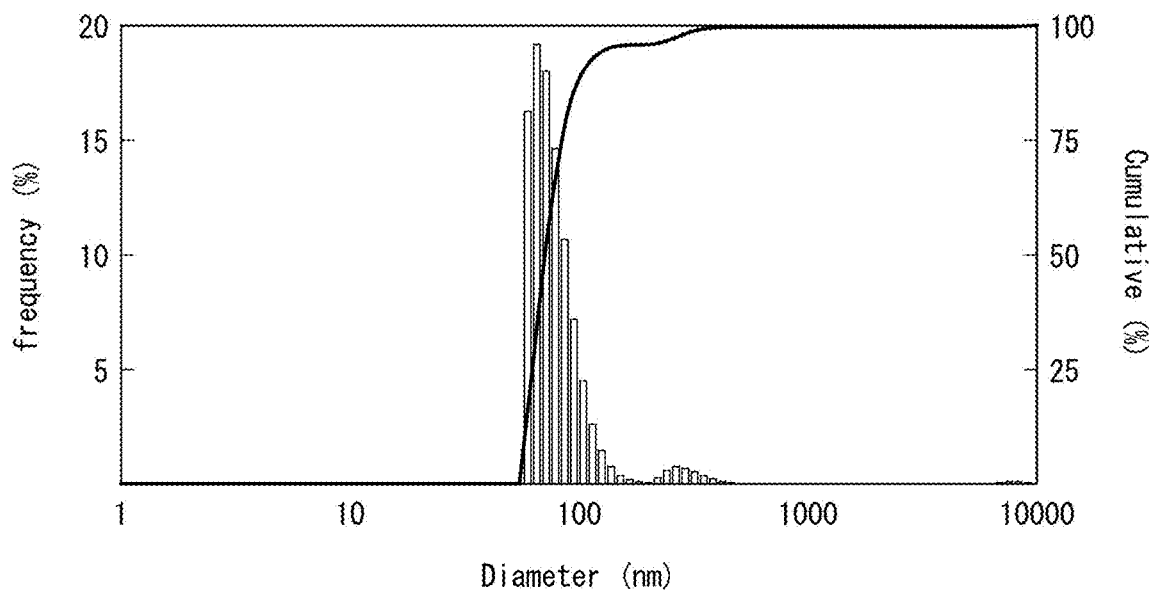
FIG. 17 is DLS data of aluminosilicate (in lamella).

From FIG. 17, it was found that no aggregation of the nanosheets occurred in the hyper-swollen lamellar phase.

<DLS Method>

Measuring device: Zeta potential measuring system ELSZ-2000, manufactured by Otsuka Electronics Sample Preparation:

Solvent: ethanol

Sample concentration: 0.05 wt %

Sample processing: approximately 30 minutes ultrasonication

Example 11

<Evaluation of Aggregation State of Aluminosilicate Nanosheets after Centrifugation>

In Example 1, the precipitate collected by centrifugation was used, and the aggregation state was evaluated by the DLS method. The results are shown in FIG. 18.

Figure 18:
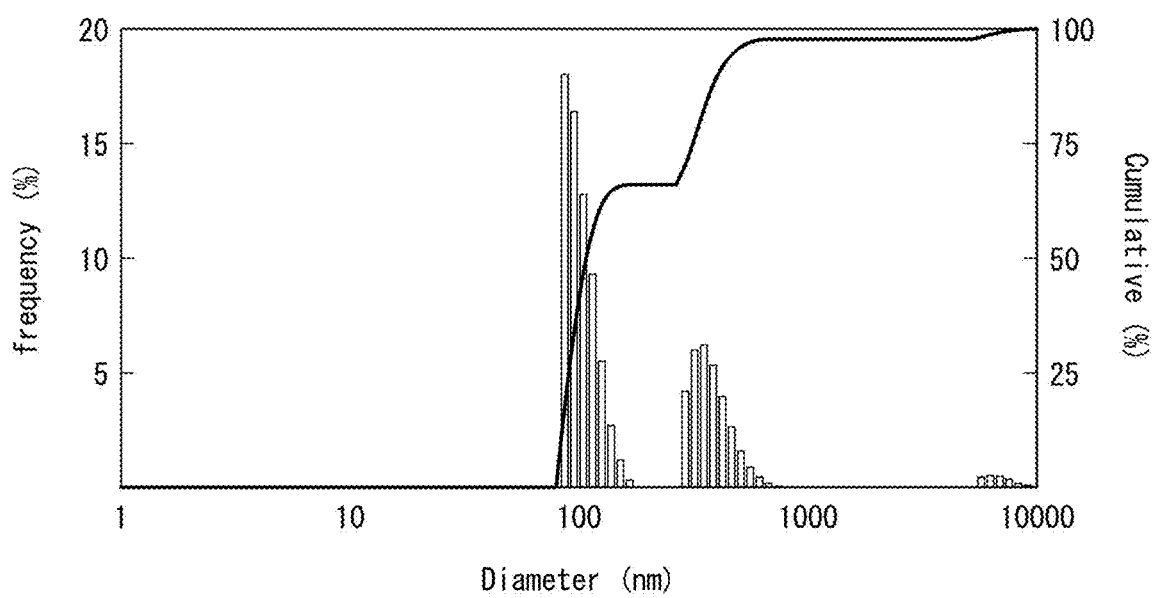
FIG. 18 is DLS data of aluminosilicate (after centrifugation).

From FIG. 18, aggregates were observed after centrifugation.

Example 12

<Evaluation of Aggregation State of Aluminosilicate Nanosheets after Filtration>

From the sample for the DLS evaluation, 2.5 ml was taken using a top syringe, and the collected sample was filtered through a Sartorius Syringe Filter (17593 K, 1.2 µm pore size), and the collected filtrate was evaluated for aggregation in the same manner as in Example 10. The results are shown in FIG. 19.

Figure 19:
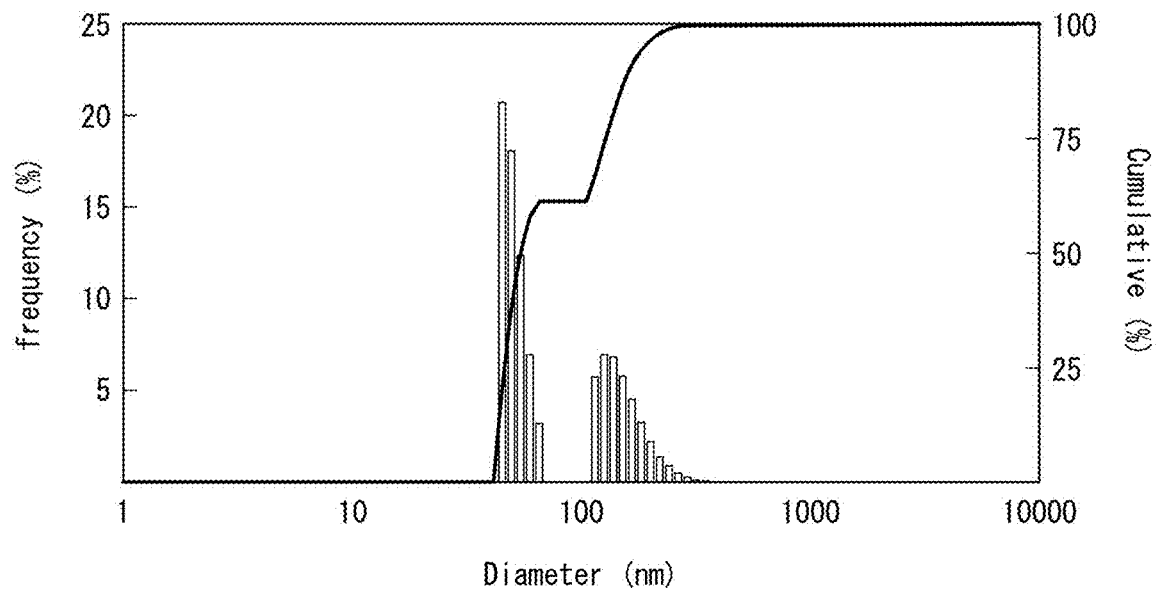
FIG. 19 is DLS data of aluminosilicate (after filtration).

The results of FIG. 19 show that about 44% by mass of the aggregate was removed by filtration.

The following equation was used to calculate the aggregates.

[Sample Weight Before Filtration−Sample Weight After Filtration]/[Sample Weight Before Filtration]×100

Example 13

<Evaluation of Aggregation State of CHA-Type Zeolite Nanosheet>

The solid of the CHA-type zeolite nanosheet obtained in Example 2 was evaluated for the aggregation state by the DLS method. The results are shown in FIG. 20.

Figure 20:
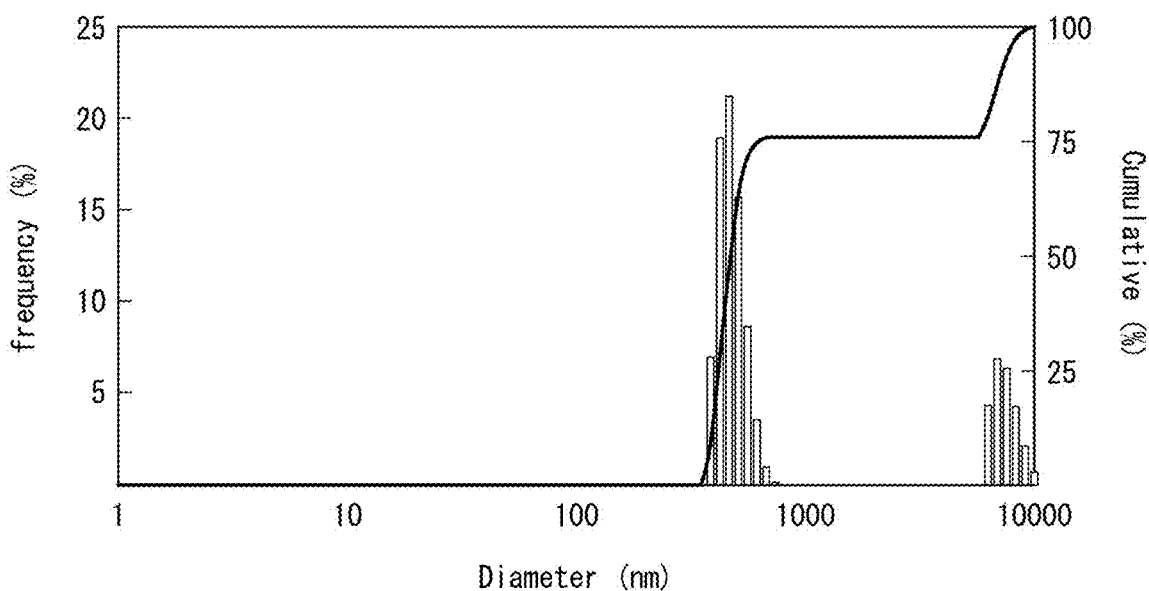
FIG. 20 is DLS data of CHA-type nanosheets.

From the results of FIG. 20, aggregates were observed when aluminosilicate nanosheets were crystallized into CHA-type zeolite nanosheets.

Example 14

<Evaluation of Aggregation State of CHA-Type Zeolite Nanosheet after One Filtration>

From the sample for the evaluation of the DLS method of Example 13, 2.5 nil was taken using a top syringe, and the collected sample was filtered through a Sartorius Syringe Filter (17593 K, 1.2 µm pore size), and the collected filtrate was evaluated for aggregation status in the same manner as in Example 13. The results are shown in FIG. 21.

Figure 21:
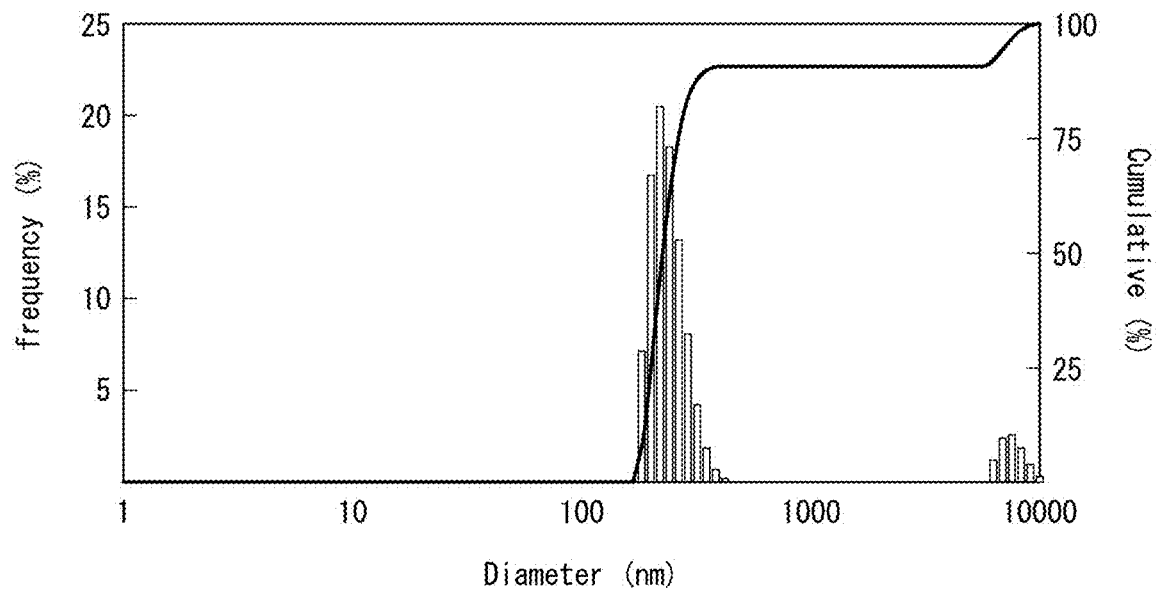
FIG. 21 is DLS data of CHA-type nanosheets (1 filtration)

From the results of FIG. 21, it was found that the amount of aggregates was reduced by 1 filtration.

Example 15

<Evaluation of Aggregation State of CHA-Type Zeolite Nanosheet after Three Filtrations>

From the sample for the evaluation by the DLS method of Example 13, 2.5 ml was taken using a top syringe, and the collected sample was filtered through a Sartorius Syringe Filter (17593 K, 1.2 µm pore size), and the collected filtrate was further filtered 2 times, and the aggregated state was evaluated using the DLS method in the same manner as in Example 13. The results are shown in FIG. 22.

Figure 22:
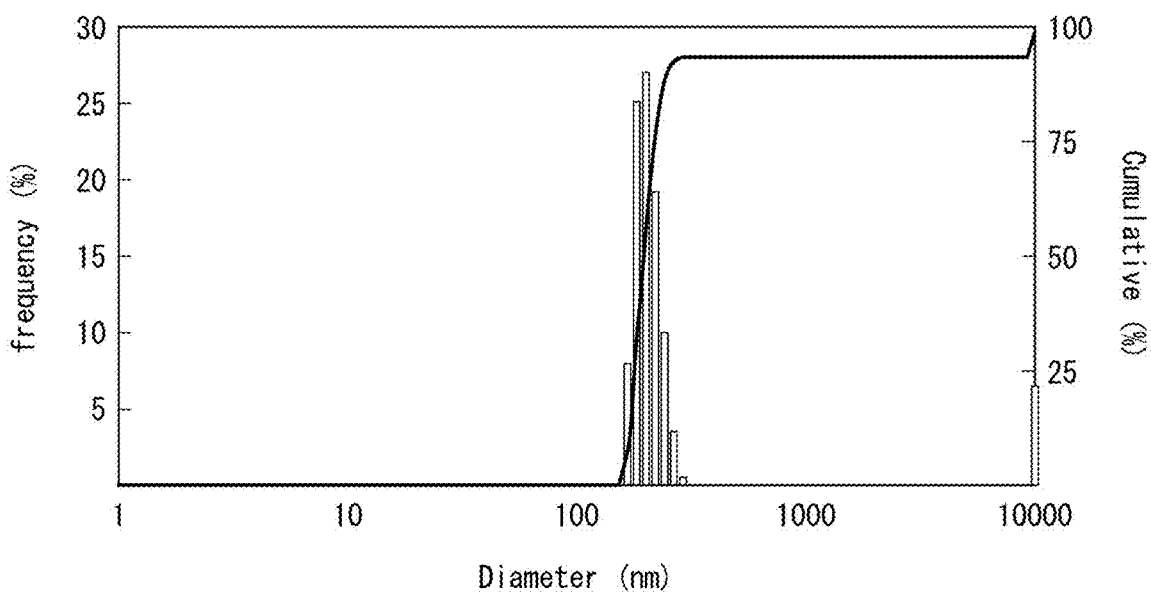
FIG. 22 is DLS data of CHA-type nanosheets (3 filtrations).

From the results of FIG. 22, it was found that 58% by mass of the aggregate was removed by 3 filtrations.

The calculation method of the aggregate is the same as in Example 12.

Example 16

<Evaluation of Aggregation State of SOD-Type Zeolite Nanosheet>

An aggregated state of the solid of the SOD zeolite nanosheet obtained in Example 5 was evaluated by the DLS method. The results are shown in FIG. 23.

Figure 23:
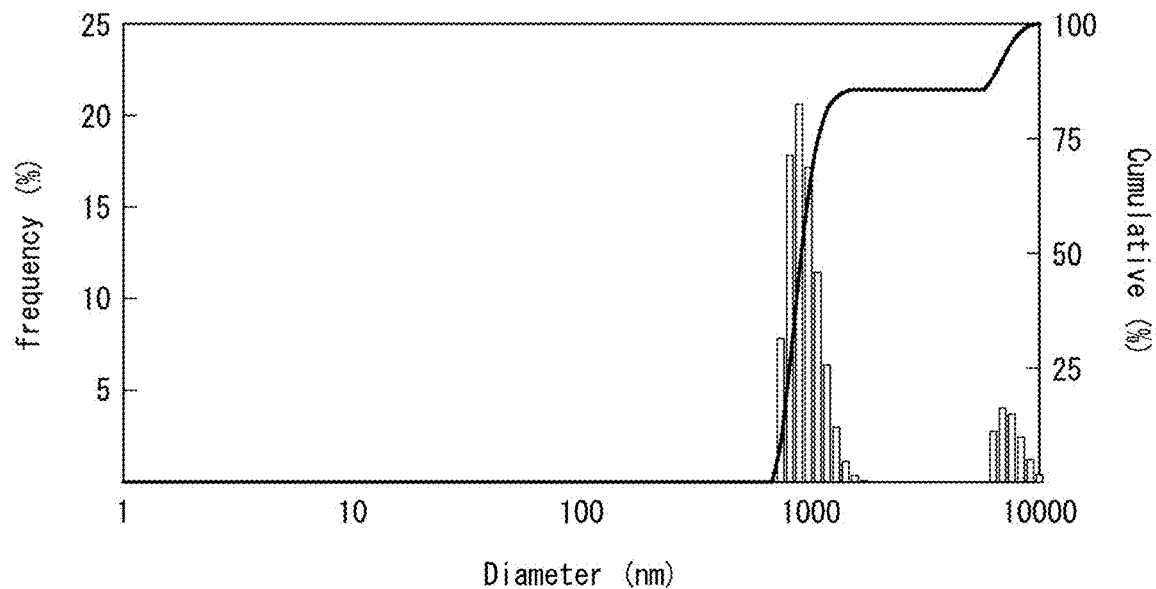
FIG. 23 is DLS data of SOD-type nanosheets.

From the results of FIG. 23, aggregates were observed when crystallization was performed from aluminosilicate nanosheets to SOD-type zeolite nanosheets.

Example 17

<Evaluation of Aggregation State of SOD-Type Nanosheets after Filtration>

From the sample for the evaluation of the DLS method of Example 16, 2.5 ml was taken using a top syringe, and the collected sample was filtered through a Sartorius Syringe Filter (17593 K, 1.2 µm pore size), and the collected filtrate was evaluated for aggregation state in the same manner as in Example 16. The results are shown in FIG. 24.

Figure 24:
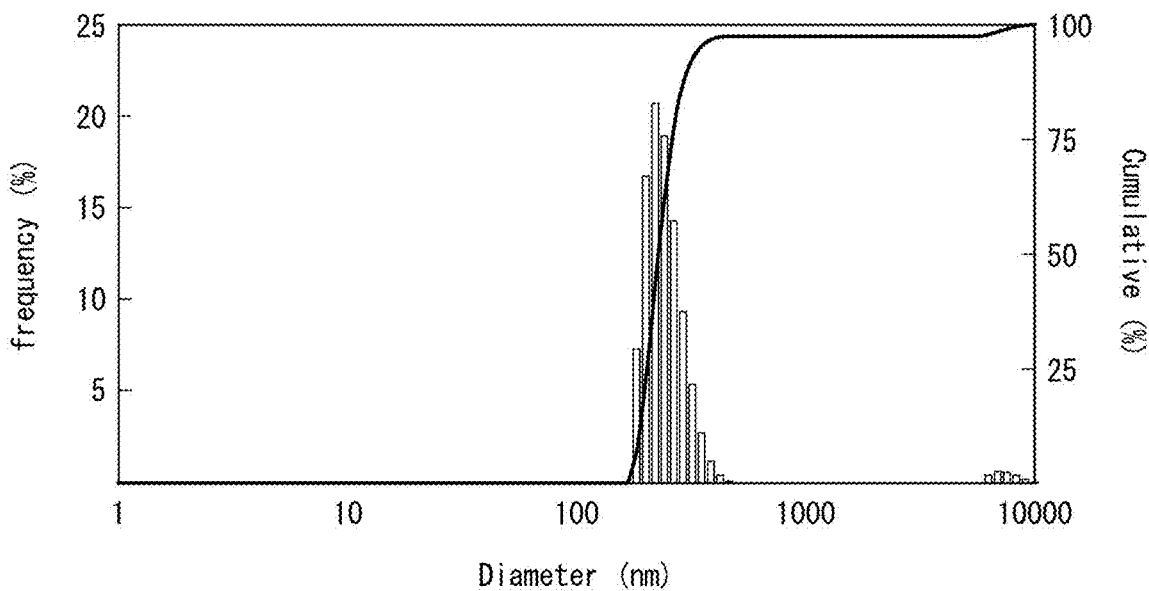
FIG. 24 is DLS data of SOD-type nanosheets (after filtration).

From the results of FIG. 24, it was found that the amount of aggregates was reduced by filtration.

Example 18

<Evaluation of Aggregation State of MFI-Type Zeolite Nanosheets>

The solid of the MFI zeolite nanosheet obtained in Example 4 was evaluated for the aggregation state by the DLS method. The results are shown in FIG. 25.

Figure 25:
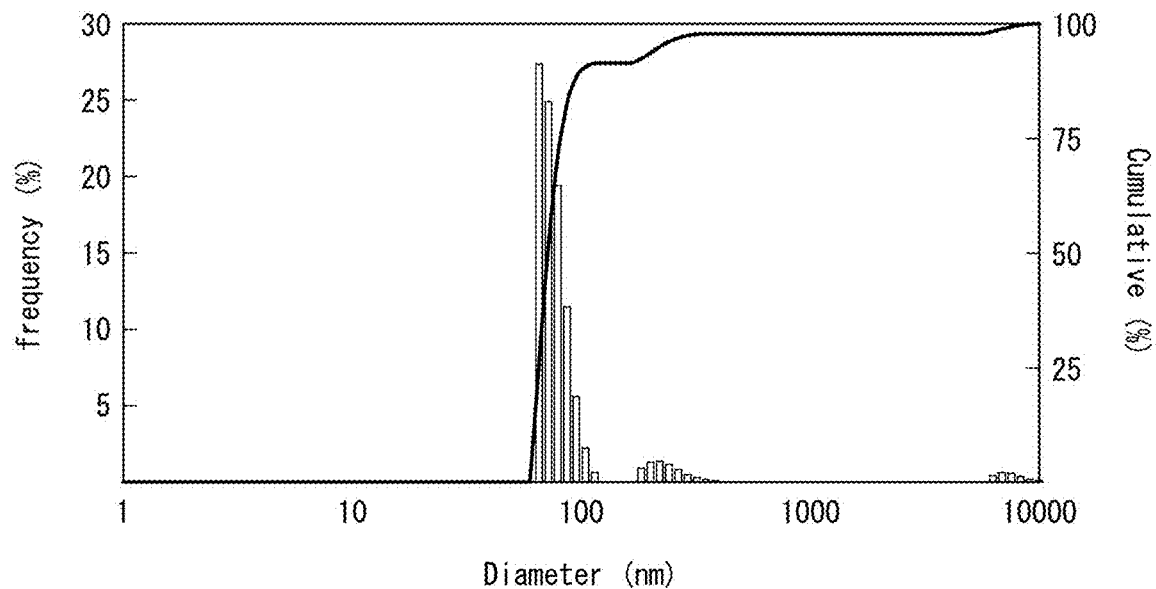
FIG. 25 is DLS data of an MFI-type nanosheet.

From the results of FIG. 25, it was found that there were substances which aggregated during crystallization.

Example 19

<Evaluation of Aggregation State of MFI-Type Zeolite Nanosheet after Filtration>

From the sample for the evaluation of the DLS method of Example 18, 2.5 ml was taken using a top syringe, and the collected sample was filtered through a Sartorius Syringe Filter (17593 K, 1.2 µm pore size), and the collected filtrate was evaluated for aggregation state in the same manner as in Example 18. The results are shown in FIG. 26.

Figure 26:
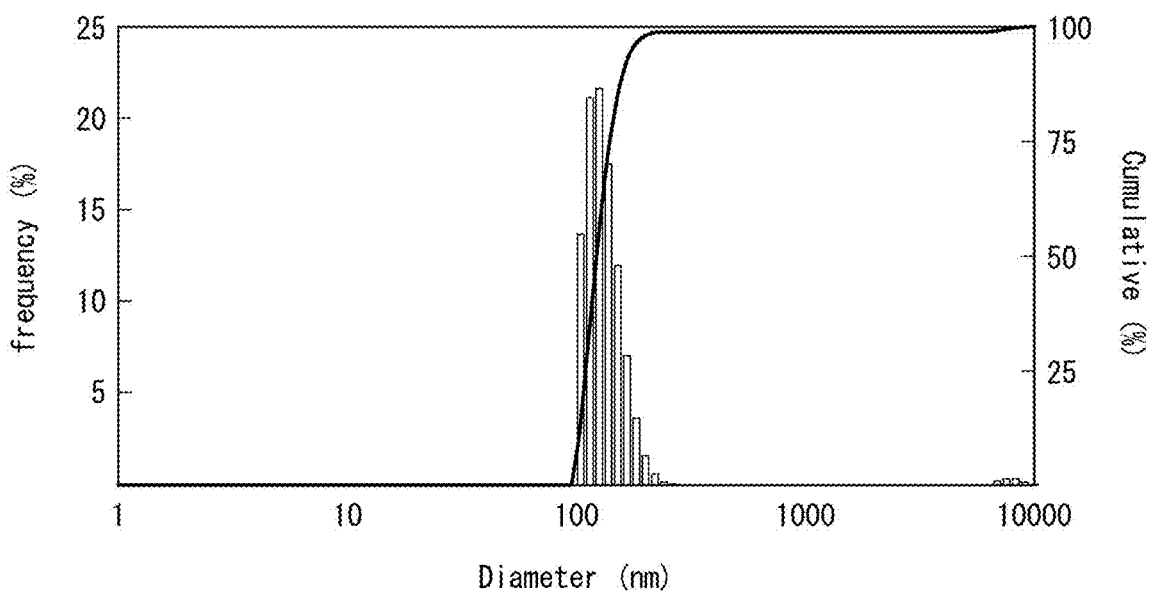
FIG. 26 is DLS data of MFI-type nanosheets (after filtration).

From the results of FIG. 26, it was found that the amount of aggregates was reduced by filtration.

<Discussion of Examples 10 to 19>

From the DLS evaluation results of Examples 10 to 19, no aggregation was observed in the hyper-swollen lamellar phase. After centrifugation, aggregates were observed, but they could be removed by filtration.

Agglomeration also occurred when zeolite was converted from aluminosilicate nanosheets to zeolite nanosheets. However, it was found that these aggregates could be removed by filtration.

Example 20

<ATO (Acetone to Olefins) Reaction>

Figure 27:
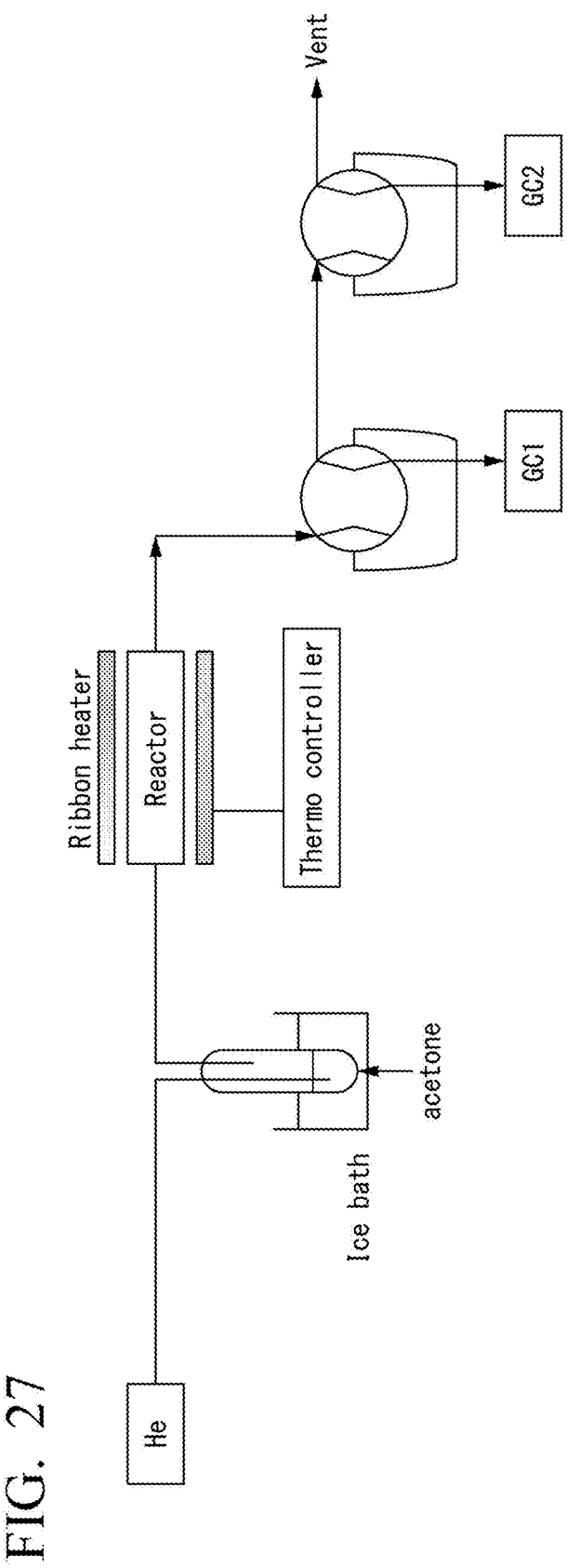
FIG. 27 is a schematic diagram showing a gas line for the reaction of acetone with olefins.

The ATO reaction test of the present example was carried out using an atmospheric pressure fixed bed reactor shown in FIG. 27. The atmospheric pressure fixed bed reactor includes a catalyst layer. Here, the ATO reaction means a reaction of acetone to olefins.

<Preparation of Catalyst for ATO Reaction>

The powder containing the CHA-type zeolite nanosheet obtained in Example 9 was used as a catalyst. A catalyst layer was prepared by uniformly packing glass beads and the catalyst into a quartz tube having an inner diameter of 4 mm and fixing the glass beads with glass wool.

<ATO Reaction>

First, acetone was bubbled with helium. A vapor mixture of acetone and helium was passed through a reactor having the catalyst layer and was reacted with the zeolite nanosheet of the present invention or zeolite of a bulk sample under the following reaction conditions. The product was then analyzed by gas chromatography.

<Reaction Conditions>

Reaction temperature: 400° C.
Amount of catalyst: 0.05 g
Helium flow rate: 1.0 ml/min
Acetone temperature: 0° C.

<Analysis of Product>

The product was analyzed by gas chromatography using Shimadzu GC-2025 (FID). Helium was used as the carrier gas.

Figure 28:
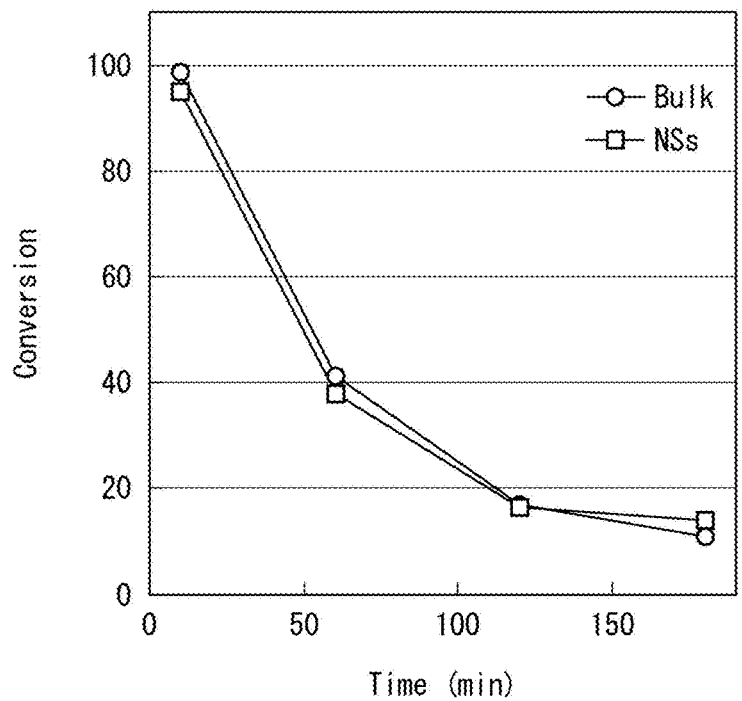
FIG. 28 shows the time course of the acetone conversion reaction between CHA-type zeolite nanosheets and bulk samples.

The change of the conversion of acetone over time was investigated. The result is shown in FIG. 28 ("NSs": the present Example using zeolite nanosheet).

The molar fractions of $C_1$-$C_4$ at 10 min elapsed time were examined. The results are shown in Table 2.

Comparative Example 1

A catalyst layer was prepared in the same manner as in Example 20 except that zeolite of a bulk sample obtained in Comparative Synthesis Example 1 was used instead of CHA-type zeolite nanosheets. The ATO reaction was carried out under the same reaction and analysis conditions as in Example 20. The product was then analyzed by gas chromatography.

The change of the conversion of acetone over time was investigated. The result is shown in FIG. 28 ("Bulk": the present Comparative Example using zeolite (CHA type) of a bulk sample).

The molar fractions of $C_1$-$C_4$ at 10 min elapsed time were examined. The results are shown in Table 2.

Discussion

From the results of FIG. 28, it was found that there was almost no change in the transition of the conversion of acetone between the case of using the zeolite nanosheet of the present invention and the case of using the zeolite of the bulk sample.

Further, from the results of Table 2, it was found that there was almost no change in the catalyst life between the case of using the zeolite nanosheet of the present invention and the case of using the zeolite of the bulk sample.

As a result of confirming the products, compared with the case of using the zeolite nanosheet of the present invention and the case of using the zeolite of the bulk sample, methane and lower olefins ($C_1$, $C_2^=$, $C_3^=$) were mainly produced in the former case. On the other hand, the latter contained more paraffin (especially $C_3$) than the former.

In addition, the ratio of $C_1$ to $C_4$ in the total products formed by the conversion of acetone was 3.8% in the case of using the zeolite nanosheet of the present invention, while it was 13.8% in the case of using the zeolite of the bulk sample.

In other words, it has been found that the use of the zeolite nanosheet of the present invention facilitates the formation of compounds larger than $C_4$.

TABLE 2

|  | $C_1$ | $C_2$ | $C_2^=$ | $C_3$ | $C_3^=$ | $C_4$ | $C_4^=$ |
|---|---|---|---|---|---|---|---|
| Nanosheets of the present invention | 7.1 | 2.5 | 20.1 | 18.5 | 26.6 | 3.4 | 21.7 |
| Bulk sample | 3.2 | 3.7 | 10.1 | 42.9 | 13.8 | 7.4 | 18.9 |

Example 21

<MTO (Methanol to Olefins) Reaction>

The MTO reaction test of the present embodiment was performed using an atmospheric pressure fixed bed reactor shown in FIG. 29. The atmospheric pressure fixed bed reactor includes a catalyst layer containing a CHA-type zeolite nanosheet. Here, the MTO reaction means a reaction of methanol to olefins.

<Preparation of Catalyst for MTO Reaction>

The powder containing the CHA-type zeolite nanosheet obtained in Example 9 was used as a catalyst. A catalyst layer was prepared by uniformly packing glass beads and the catalyst into a quartz tube having an inner diameter of 4 mm and fixing the glass beads with glass wool.

<MTO Reaction>

First, methanol was bubbled with helium. A vapor mixture of methanol and helium was passed through a reactor equipped with the catalyst layer and was reacted with the zeolite sheet of the present invention or zeolite of a bulk sample under the following reaction conditions. The products were then analyzed by gas chromatography.

<Reaction Conditions>

Reaction temperature: 400° C.
Amount of catalyst: 0.025 g
Helium flow rate: 7.5 ml/min
Methanol temperature: 10° C.

<Analysis of Products>

The product was analyzed by gas chromatography using Shimadzu GC-2025 (FID). Helium was used as the carrier gas.

The change of conversion of methanol over time was investigated. The results are shown in FIG. 30.

The molar fractions of $C_1$-$C_4$ at 10 min elapsed time were examined. The results are shown in Table 3.

Comparative Example 2

A catalyst layer was prepared in the same manner as in Example 21 except that zeolite of a bulk sample obtained in Comparative Synthesis Example 1 was used instead of CHA-type zeolite nanosheets. The reaction was carried out under the same reaction and analysis conditions as in Example 21. The product was then analyzed by gas chromatography.

The change of conversion of methanol over time was investigated. The results are shown in FIG. 30.

The molar fractions of $C_1$-$C_4$ at 10 min elapsed time were examined. The results are shown in Table 3.

Discussion

From the results of FIG. 30, when the zeolite nanosheet of the present invention was used, it was found that the conversion of methanol after 60 minutes and thereafter was lower than that when the zeolite of the bulk sample was used.

Further, from the results of Table 3, comparing the case of using the zeolite nanosheet of the present invention and the case of using the zeolite of the bulk sample, it was found that the catalyst life of the former was slightly shorter than that of the latter.

As a result of confirming the products, comparing the case using the zeolite nanosheet of the present invention and the case of using the zeolite of the bulk sample, $C_2^=$, $C_3$, and $C_3^=$ were produced more in the former than in the latter. On the other hand, regarding the products larger than $C_4$, the latter showed a greater proportion than the former.

In addition, the ratio of $C_1$ to $C_4$ in the total product formed by methanol conversion was 45% in the case of using the zeolite nanosheet of the present invention, while it was 41% in the case of using the zeolite of the bulk sample.

In other words, it was found that the presence ratio of $C_1$ to $C_4$ increased by using the zeolite nanosheet of the present invention.

TABLE 3

|  | $C_1$ | $C_2$ | $C_2^=$ | $C_3$ | $C_3^=$ | $C_4$ | $C_4^=$ |
|---|---|---|---|---|---|---|---|
| Nanosheets of the present invention | 1.6 | 2.5 | 23.8 | 22.8 | 35.6 | 2.3 | 11.4 |
| Bulk sample | 1.5 | 2.0 | 31.3 | 10.4 | 39.8 | 1.3 | 13.6 |

Example 22

<PPTO (Propane to Olefins) Reaction>

The PPTO reaction test of the present example was carried out using an atmospheric pressure fixed bed reactor shown in FIG. 31. The atmospheric pressure fixed bed reactor includes a catalyst layer containing a CHA-type zeolite nanosheet. Here, the PPTO reaction means the reaction of propane to olefins.

<Preparation of Catalyst for PPTO Reaction>

The powder containing the CHA-type zeolite nanosheet obtained in Example 9 was used as a catalyst. A catalyst layer was prepared by uniformly packing glass beads and the catalyst into a quartz tube having an inner diameter of 4 mm and fixing the glass beads with glass wool.

<PPTO Reaction>

First, helium and propane were mixed in the flow channel. The mixed gas of helium and propane was passed through a reactor equipped with the catalyst layer and was reacted with the zeolite of zeolite nanosheet of the present invention or zeolite of a bulk sample under the following reaction conditions. The product was then analyzed by gas chromatography.

<Reaction Conditions>
Reaction temperature: 400° C.
Amount of catalyst: 0.05 g
Helium flow rate: 6.4 ml/min
Propane flow rate: 3.0 ml/min <Analysis of Products>

The product was analyzed by gas chromatography using Shimadzu GC-2025 (FID). Helium was used as the carrier gas.

The change of conversion of propane over time was investigated. The results are shown in FIG. 32.

Comparative Example 3

A catalyst layer was prepared in the same manner as in Example 22 except that zeolite of a bulk sample obtained in Comparative Synthesis Example 1 was used instead of CHA-type zeolite nanosheets. The PPTO reaction was carried out under the same reaction and analysis conditions as in Example 22. The product was then analyzed by gas chromatography.

The change of conversion of propane over time was investigated. The results are shown in FIG. 32.

Discussion

From the result of FIG. 32, it was found that there was almost no reaction between the case of using the zeolite nanosheet of the present invention and the case of using the zeolite of the bulk sample. It was found that at the reaction temperature of 400° C., paraffin unlikely reacted at both the acid sites in the pores and the acid sites on the outer surface.

Example 23

<PLTO (Propylene to Olefins) Reaction>

The PLTO reaction test of the present example was carried out using an atmospheric pressure fixed bed reactor shown in FIG. 33. The atmospheric pressure fixed bed reactor includes a catalyst layer containing a CHA-type zeolite nanosheet. Here, the PLTO reaction means a reaction of propylene to olefins.

<Preparation of Catalyst for PLTO Reaction>

The powder containing the CHA-type zeolite nanosheet obtained in Example 9 was used as a catalyst. A catalyst layer was prepared by uniformly packing glass beads and the catalyst into a quartz tube having an inner diameter of 4 mm and fixing the glass beads with glass wool.

<PLTO Reaction>

First, helium and propylene were mixed in the flow channel. The mixed gas of helium and propylene was passed through a reactor equipped with the catalyst layer and was reacted with the zeolite nanosheet of the present invention or zeolite of a bulk sample under the following reaction conditions. The product was then analyzed by gas chromatography.

<Reaction Conditions>
Reaction temperature: 400° C.
Amount of catalyst: 0.05 g
Helium flow rate: 6.4 ml/min
Propylene flow rate: 3.0 ml/min <Analysis of Products>

The product was analyzed by gas chromatography using Shimadzu GC-2025 (FID). Helium was used as the carrier gas.

The change of conversion of propylene over time was investigated. The results are shown in FIG. 34.

The molar fractions of $C_1$-$C_4$ at 10 min elapsed time were investigated. The results are shown in Table 4.

Comparative Example 4

A catalyst layer was prepared in the same manner as in Example 23 except that zeolite of a bulk sample obtained in Comparative Synthesis Example 1 was used instead of CHA-type zeolite nanosheets. The PLTO reaction was carried out under the same reaction and analysis conditions as in Example 23. The product was then analyzed by gas chromatography.

The change of conversion of propylene over time was investigated. The results are shown in FIG. 34.

The molar fractions of $C_1$-$C_4$ at 10 min elapsed time were examined. The results are shown in Table 4.

Discussion

From the results of FIG. 34, it was found that there was almost no change in the catalyst life between the case of using the zeolite nanosheet of the present invention and the case of using the zeolite of the bulk sample.

As a result of confirming the products from the results of Table 4, comparing the case of using the zeolite nanosheet of the present invention with the case of using the zeolite of the bulk sample, the former produced a larger amount of olefin than the latter. On the other hand, the latter contained more paraffin than the former.

The ratio of $C_1$ to $C_4$ in the total product formed by the conversion of propylene was 24% in the case of using the zeolite nanosheet of the present invention, while it was 17% in the case of using the zeolite of a bulk sample.

That is, it was found that there was almost no difference in reactivity between the case of using the zeolite nanosheet of the present invention and the case of using the zeolite of the bulk sample.

TABLE 4

|  | $C_1$ | $C_2$ | $C_2^-$ | $C_3$ | $C_3^-$ | $C_4$ | $C_4^-$ |
|---|---|---|---|---|---|---|---|
| Nanosheets of the present invention | 0.5 | 0.4 | 30.3 | 16.6 |  | 1.1 | 51.2 |
| Bulk sample | 1.0 | 2.3 | 43.2 | 18.1 |  | 1.4 | 34.1 |

Example 24

"Effect of Polyethylene Decomposition Temperature Reduction by Addition of Zeolite Nanosheet"

The effect of lowering the LDPE decomposition temperature by adding the CHA-type zeolite nanosheet obtained in Example 9 to low-density polyethylene (LDPE) was confirmed by the following procedure.

[1] 0.008 g of LDPE and 0.02 g of the CHA-type zeolite nanosheet obtained in Example 9 were physically mixed in a mortar.

[2] The mixture obtained above was placed on a Petri dish which was heated to about 110° C.

[3] The mixture softened by heating was crushed.

[4] The flattened mixture was folded in half.

[5] Steps 3 and 4 above were repeated about 10 times (pie kneading conversion).

[6] A sample for evaluation was obtained by cooling the mixture obtained above.

[7] Using approximately 2 mg of the sample obtained above for evaluation, TG, DTA, Conversion, and DTG were measured using DTG-60 (manufactured by Shimadzu Corporation) which is a simultaneous thermogravimetry-differential thermal analysis (TG/DTA) measurement device.

Measurement Program: heating from room temperature to 120° C. at a rate of 10° C./min, then maintaining at 120° C. for 6 hours, followed by heating to 800° C. at a rate of 10° C./min.

The results of TG, DTA, Conversion, and DTG are shown in FIGS. 35 to 38, respectively. (Each is indicated by thin lines. CHA-NSs: the present example of adding CHA-type zeolite nanosheets to low-density polyethylene (LDPE).)

Comparative Example 5

TG, DTA, Conversion, and DTG were measured by the same method as in Example 24 except that zeolite (CHA type) of a bulk sample obtained in Comparative Synthesis Example 1 was used instead of the CHA-type zeolite nanosheet in Example 24, and the results are shown in FIGS. 35 to 38. (Each is indicated by dotted lines. "Bulk": A comparative example in which a zeolite (CHA type) of a bulk sample is added to a low-density polyethylene (LDPE).)

Comparative Example 6

TG, DTA, Conversion, and DTG were measured by the same method as in Example 24 except that only LPDE was used without adding CHA-type zeolite nanosheets of Example 24, and the results are shown respectively in FIGS. 35 to 38. (Each is indicated by bold lines. "LDPE": the present comparative example of only low-density polyethylene (LDPE) without the addition of zeolite.)

Example 25

"Effect of Polyethylene Decomposition Temperature Reduction by Addition of Zeolite Nanosheet"

The effect of lowering the decomposition temperature of low-density polyethylene (LDPE) by adding the CHA-type zeolite nanosheet obtained in Example 15 to LDPE was confirmed by the following procedure.

1. LDPE 0.008 g and the CHA-type zeolite nanosheet 0.02 g obtained in Example 15 were mixed at a ratio of 15% by mass.

2. 300 μml of toluene was added to the resulting mixture.

3. LDPE was dissolved in toluene by heating the resulting mixture.

4. The mixture thus obtained was subjected to ultrasonic treatment.

5. A sample for evaluation was obtained by evaporating toluene from the mixture liquid obtained after the ultrasonic treatment.

6. Using about 2 mg of the sample obtained above for evaluation, TG, DTA, Conversion, and DTG were measured using DTG-60 (manufactured by Shimadzu Corporation) which is a TG/DTA simultaneous measuring device.

Measurement Program: heating from room temperature to 799° C. at a rate of 5° C./min The results of TG, DTA, Conversion, and DTG are shown in FIGS. 35 to 38, respectively. (Each is indicated by thin lines. CHA-NSs: the present Example of adding CHA-type zeolite nanosheets to low-density polyethylene (LDPE).)

Comparative Example 7

TG, DTA, Conversion, and DTG were measured by the same method as in Example 25 except that the zeolite (CHA type) of a bulk sample obtained in Comparative Synthesis Example 1 was used instead of the CHA-type zeolite nanosheet in Example 25, and the results are shown in FIGS. 39 to 42. (Each is indicated by dotted lines. "Bulk": A comparative example in which the zeolite (CHA type) of a bulk sample is added to a low-density polyethylene (LDPE).)

Comparative Example 8

TG, DTA, Conversion, and DTG were measured by the same method as in Example 25 except that only LPDE was used without adding CHA-type zeolite nanosheets of Example 25, and the results are shown respectively in FIGS. 39 to 42. (Each is indicated by bold lines. "LDPE": the present comparative example in which only low-density polyethylene (LDPE) was used, without the addition of zeolite.)

Discussion

From FIG. 35, in Example 24, Comparative Example 5, and Comparative Example 6, the temperatures at the point when 90% is reached are 426.7° C., 428.9° C., and 440.7° C., respectively. The lowest temperature was shown in Example 24 using LDPE in which the CHA-type zeolite nanosheet was added.

From FIG. 36, in Example 24, Comparative Example 5, and Comparative Example 6, the peak positions were 455.9° C., 466.1° C., and 471.9° C., respectively. The lowest temperature was shown in Example 24 using LDPE in which the CHA-type zeolite nanosheet was added.

From FIG. 37, in Example 24, Comparative Example 5, and Comparative Example 6, the temperatures at the point when 10% is reached are 426.7° C., 428.9° C., and 440.7° C., respectively. The lowest temperature was shown in Example 24 using LDPE in which the CHA-type zeolite nanosheet was added.

From FIG. 38, in Example 24, Comparative Example 5, and Comparative Example 6, the peak positions were 455.9° C., 468.1° C., and 473.9° C., respectively. The lowest temperature was shown in Example 24 using LDPE in which the CHA-type zeolite nanosheet was added.

From FIG. 39, in Example 25, Comparative Example 7, and Comparative Example 8, the temperatures at the point of reaching 90% were 398.9° C., 402.4° C., and 442.7° C., respectively. The lowest temperature was shown in Example 25 using LDPE in which the CHA-type zeolite nanosheet was added.

From FIG. 40, in Example 25, Comparative Example 7, and Comparative Example 8, the peak positions were 455.9° C., 466.1° C., and 471.9° C., respectively. The lowest temperature was shown in Example 25 using LDPE in which the CHA-type zeolite nanosheet was added.

From FIG. 41, in Example 25, Comparative Example 7, and Comparative Example 8, the temperatures at the point of reaching 10% were 396.1° C., 399.4° C., and 442.7° C. respectively. The lowest temperature was shown in Example 25 using LDPE in which the CHA-type zeolite nanosheet was added.

From FIG. 42, in Example 25, Comparative Example 7, and Comparative Example 8, the peak positions were 431° C., 446.7° C., and 473.3° C., respectively. The lowest temperature was shown in Example 25 using LDPE in which the CHA-type zeolite nanosheet was added.

From the above results, it was confirmed that the thermal decomposition temperature of LDPE was lowered by the addition of the CHA-type zeolite nanosheet.

The invention claimed is:

1. A method for producing sheet-like particles of zeolite, comprising:
    a first step which comprises
        forming a bilayer in a solvent,
        forming a hyper-swollen lamellar phase of the bilayer by adding, in the solvent, an aluminum atomic source, and at least one atomic source selected from the group consisting of a silicon atomic source and a phosphorus atomic source, and
        forming sheet-like particles of a precursor of zeolite between two monomolecular layers, wherein the two monomolecular layers constitute the bilayer and are formed from amphiphilic molecules; and
    a second step of bringing the sheet-like particles of the precursor of zeolite into contact with gaseous water in a container to form the sheet-like particles of zeolite,
    wherein a thickness of the sheet-like particles of the zeolite is 1 nm or more and 100 nm or less;
    an aspect ratio (maximum width/thickness in particles) of the sheet-like particles of the zeolite is 100 or more;
    the solvent contained in a whole system in the formation of the hyper-swollen lamellar phase is a mixed solvent containing a hydrocarbon solvent and water, wherein the whole system in the formation of the hyper-swollen lamellar phase means any components which are mixed in order to form the super-swollen lamellar phase and include solutes and solvents; and
    a mass ratio of the hydrocarbon-containing solvent and water in the mixed solvent is 85:15 to 99.99:0.01.

2. The method for producing the sheet-like particles of zeolite according to claim 1,
    wherein a mass ratio of the solvent to whole system in formation of the hyper-swollen lamellar phase is 90% by mass or more.

3. The method for producing the sheet-like particles of zeolite according to claim 1,
    wherein an amount of water contained in the solvent is 5% by mass or less.

4. The method for producing the sheet-like particles of zeolite according to claim 1,
    wherein in the second step, contacting with gaseous water is carried out in the presence of a structure-directing agent.

5. The method for producing the sheet-like particles of zeolite according to claim 1,
    wherein the sheet-like particles of zeolite have a structure represented by "SOD", "PHI", "CHA", or "MFI", each of which is a structural code of the International Zeolite Association (IZA).

6. The method for producing the sheet-like particles of zeolite according to claim 1,
    wherein the sheet-like particles of the precursor of zeolite are present in a hyper-swollen lamellar phase in a state where the sheet-like particles are not substantially agglomerated.

7. The method for producing the sheet-like particles of zeolite according to claim 1,
wherein a thickness of the sheet-like particles of the precursor of zeolite is 1 nm or more and 100 nm or less, and
an aspect ratio (maximum particle width/particle thickness) of the sheet-like particles of the precursor of zeolite is 100 or more.

8. The method according to claim 1, wherein the zeolite is aluminosilicate.

* * * * *